US008017637B2

(12) United States Patent
Galcera-Contour et al.

(10) Patent No.: US 8,017,637 B2
(45) Date of Patent: Sep. 13, 2011

(54) INHIBITORS OF CDC PHOSPHATASES

(75) Inventors: Marie-Odile Galcera-Contour, Bondoufle (FR); Dennis Bigg, Gif sur Yvette (FR); Grégoire Prevost, Antony (FR); Alban Sidhu, Palaiseau (FR)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 861 days.

(21) Appl. No.: 11/722,075

(22) PCT Filed: Dec. 16, 2005

(86) PCT No.: PCT/FR2005/003161
§ 371 (c)(1),
(2), (4) Date: Jun. 18, 2007

(87) PCT Pub. No.: WO2006/067311
PCT Pub. Date: Jun. 29, 2006

(65) Prior Publication Data
US 2009/0275624 A1 Nov. 5, 2009

(30) Foreign Application Priority Data
Dec. 17, 2004 (FR) ..................... 04 13456

(51) Int. Cl.
*A61K 31/428* (2006.01)
*A61K 31/423* (2006.01)
*C07D 417/12* (2006.01)
*C07D 413/12* (2006.01)
*C07D 417/14* (2006.01)

(52) U.S. Cl. ......... 514/367; 548/219; 548/156; 514/375

(58) Field of Classification Search .................. 514/367, 514/375; 548/219, 156
See application file for complete search history.

(56) References Cited

U.S. PATENT DOCUMENTS

| 5,523,430 | A | 6/1996 | Patel et al. |
| 7,279,467 | B2 | 10/2007 | Galcera Contour et al. |
| 7,335,674 | B2 | 2/2008 | Galcera Contour et al. |
| 2006/0135573 | A1 | 6/2006 | Galcera Contour et al. |
| 2006/0281736 | A1 | 12/2006 | Prevost et al. |
| 2007/0293487 | A1 | 12/2007 | Galcera Contour et al. |

FOREIGN PATENT DOCUMENTS

| GB | 1 534 275 | 11/1978 |
| WO | 97/30053 | 2/1997 |
| WO | 01/34203 | 5/2001 |
| WO | 01/45680 | 6/2001 |
| WO | 03/050098 | 6/2003 |
| WO | 03/055868 | 7/2003 |
| WO | WO03/055868 A1 | 7/2003 |
| WO | 2005/000843 | 1/2005 |
| WO | 2005/000852 | 1/2005 |
| WO | 2006/051202 | 5/2006 |
| WO | 2006/067311 | 6/2006 |
| WO | WO2006/067311 A3 | 6/2006 |

OTHER PUBLICATIONS

Berge et al. J. Pharm. Sci. 1997, 66, pp. 1-19.*
Luo et al. Cell 2009, 136, 823-837.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Ryu et al., "Synthesis and Antifungal Activities of 5/6-arylamino-4,7-Dioxobenzothiazoles", Bio-Organic and Medicinal Chemistry Letters, vol. 10, No. 14, pp. 1589-1591, (Jul. 17, 2000).
Ryu et al., "5-Arylamino-2-methyl-4,7 Dioxobenzothiazoles as Inhibitors of Cyclin-Dependent Kinase 4 and Cytocoxic Agents", Bio-Organic and Medicinal Chemistry Letters, vol. 10, No. 5, pp. 461-464, (Mar. 5, 2000).
Lyon et al., "Synthesis and Structure Verification of an Analogue of Kuanoniamine A," J.Chem. Soc. Perkin Transactions 1: Organic and BioOrganic Chemistry, vol. 4; pp. 437-442 (1999).
Kristjansdottir et al., "Cdc25 Phosphatases and Cancer", Chemistry and Biology, vol. 11, pp. 1043-1051 (Aug. 2004).
Ryu et al., "Modulation of NAD(P)H: Quinone Qxidoreductase (NQO1) Activity Mediated by 5-arylamino-2-methyl-4-7-Dioxobenzothiazoles and their Cytotoxic Potential", Archives of Pharmacal Research, vol. 23, issue 6, pp. 554-558 (2000).
Eckstien, J.W., "Cdc25 as a Potential Target of Anticancer Agents" Investigational New Drugs, vol. 18, pp. 149-156, Figure 3a (2000).
McCain, D.F. et al., Suramin Derivatives as Inhibitors and Activators of Protein-Tyrosine Phosphates, Jpurnal of Biological Chemistry, vol. 129, No. 15, pp. 14713-14725, Figures 2-6 (Jan. 2004).
Talaga, P. et al., "Synthesis of Boc-Cys_Ala_OMe and its Stereoselective Addiction to α-Methylene-γ-Butrolactones", Tetrahedron, vol. 45, No. 16, pp. 5029-5038 (1989).
Zhu, X. et al. "Synthesis of S-Linked Glycopeptides in Aqueos Solution". J. Org. Chem., vol. 68, No. 14, pp. 5641-5651, XP002326455, Schema 1 (2003).
Golub et al., "Molecular Classification of Cancer: Class Discovery and Class Prediction by Gene Expression Monitoring", Science, vol. 286, pp. 531-537 (1999).
Hortobagyi, G. "Treatment of Breast Cancer", N. Engl., J. Med, 339, pp. 974-984 (1998).
Preliminary Amendment filed Jun. 18, 2007 in Co-pending U.S. Appl. No. 11/722,075.

(Continued)

*Primary Examiner* — Joseph Kosack
*Assistant Examiner* — Matthew Coughlin
(74) *Attorney, Agent, or Firm* — Hunton & Williams LLP

(57) ABSTRACT

A subject of the present invention is novel compounds comprising 2 or 3 benzothiazole-4,7-dione- or benzooxazole-4,7-dione-type units, which inhibit the cdc25 phosphatases, in particular cdc25-C phosphatase. These compounds can in particular be used in the treatment of cancer.

24 Claims, No Drawings

OTHER PUBLICATIONS

International Preliminary Report on Patentability (Form PCT/IPEA/409) in International Application No. PCT/FR2005/002763 (WO 06/051202), 2007.

International Preliminary Report on Patentability (Form PCT/IPEA/409) in International Application No. PCT/FR02/04544 (WO 03/055868), 2004.

International Preliminary Report on Patentability (Form PCT/IPEA/409) in International Application No. PCT/FR2004/001578 (WO 05/000843), 2006.

International Preliminary Report on Patentability (Form PCT/IPEA/409) in International Application No. PCT/FR2004/001586 (WO 05/000852), 2006.

International Search Report for PCT/FR2005/003161, 2007.

Eckstein, "CDC25 as a potential target of anticancer agents," Investigational New Drugs, vol. 18, pp. 149-156, 2000 (XP002340121).

Kristjansdottir, et al., "CDC25 Phosphatases and Cancer," Chemistry & Biology, vol. 11, pp. 1043-1051, Aug. 2004 (XP002340122).

McCaint, D.F. et al., "Suramin Derivatives as Inhibitors and Activators of Protein-tyrosine Phosphatases," Journal of Biological Chemistry, vol. 279, No. 15, pp. 14713-14725, Jan. 2004 (XP002340123).

International Search Report for PCT/FR2005/003161 (English Translation), 2007.

* cited by examiner

INHIBITORS OF CDC PHOSPHATASES

CONTINUITY DATA

This application is a national stage application of PCT/FR2005/003161, filed on Dec. 16, 2005, which in turn claims priority to FR 0413456, filed on Dec. 17, 2004; both of which applications are hereby incorporated by reference in their entirety.

FIELD OF INVENTION

A subject of the present invention is novel inhibitors of cdc25 phosphatases.

BACKGROUND OF INVENTION

Control of the transition between the different phases of the cell cycle during mitosis or meiosis is ensured by a set of proteins the enzymatic activities of which are associated with different states of phosphorylation. These states are controlled by two major classes of enzymes: the kinases and the phosphatases.

The synchronization of the different phases of the cell cycle thus allows the reorganization of the cell architecture at each cycle throughout the living world (microorganisms, yeast, vertebrates, plants). Among the kinases, the cycline-dependent kinases (CDKs) play a major role in this control of the cell cycle. The enzymatic activity of these different CDKs is controlled by two other families of enzymes which work in opposition (Jessus and Ozon, *Prog. Cell Cycle Res.* (1995), 1, 215-228). The first includes kinases such as Wee1 and Mik1 which deactivate the CDKs by phosphorylating certain amino acids (Den Haese et al., *Mol. Biol. Cell* (1995), 6, 371-385). The second includes phosphatases such as Cdc25 which activate the CDKs by dephosphorylating the tyrosine and threonine residues of CDKs (Gould et al., *Science* (1990), 250, 1573-1576).

The phosphatases are classified in 3 groups: the serine/threonine phosphatases (PPases), the tyrosine phosphatases (PTPases) and the dual-specificity phosphatases (DSPases). These phosphatases play an important role in the regulation of numerous cell functions.

As regards human cdc25 phosphatases, 3 genes (cdc25-A, cdc25-B and cdc25-C) code for the cdc25 proteins. Moreover, variants originating from the alternative splicing of the gene cdc25B have been identified: these are cdc25B1, cdc25B2 and cdc25B3 (Baldin et al., *Oncogene* (1997), 14, 2485-2495).

The role of the Cdc25 phosphatases in oncogenesis is now better known and the action mechanisms of these phosphatases are illustrated in particular in the following references: Galaktionov et al., *Science* (1995), 269, 1575-1577; Galaktionov et al., *Nature* (1996), 382, 511-517; and Mailand et al., *Science* (2000), 288, 1425-1429.

The overexpression of the different forms of cdc25 is now reported in numerous series of human tumors for example:
Breast cancer: cf. Cangi et al., *Résumé* 2984, AACR meeting San Francisco, 2000);
Lymphomas: cf. Hernandez et al., *Int. J. Cancer* (2000), 89, 148-152 and Hernandez et al., *Cancer Res.* (1998), 58, 1762-1767;
Cancers of the neck and the head: cf. Gasparotto et al., *Cancer Res.* (1997), 57, 2366-2368;
Cancers of the pancreas: cf. Junchao Guo et al., *Oncogene* (2004), 23, 71-81.

Moreover, E. Sausville's group reports an inverse correlation between the level of to expression of cdc25-B in a panel of 60 lines and their sensitivities to CDK inhibitors, suggesting that the presence of cdc25 can provide resistance to certain antineoplastic agents and more particularly to CDK inhibitors (Hose et al., *Proceedings of AACR*, Abstract 3571, San Francisco, 2000).

Among other targets, compounds capable of inhibiting the Cdc25 phosphatases are currently being researched in order to use them in particular as anti-cancer agents.

The Cdc25 phosphatases also play a role in the neurodegenerative diseases such as Alzheimer's disease (cf. Zhou et al., *Cell Mol Life Sci.* (1999), 56(9-10), 788-806; Ding et al., *Am. J. Pathol.* (2000), 157(6), 1983-90; Vincent et al., *Neuroscience* (2001), 105(3), 639-50) so that it is also possible to envisage using compounds possessing an inhibition activity on these phosphatases for treating these diseases.

Another problem addressed by the invention is research into medicaments intended to prevent or treat the rejection of organ transplants or also to treat auto-immune diseases. In these disorders/diseases, the non-appropriate activation of the lymphocytes and the monocytes/macrophages is involved. Immunosuppressive medicaments known at present have side-effects which could be reduced or modified by products specifically targeting the signalling routes in the haematopoietic cells which initiate and maintain inflammation.

Firstly, a subject of the invention is novel inhibitors of cdc25 phosphatases (in particular of cdc25-C phosphatase), which are dimer-type derivatives of benzothiazole-4,7-diones and benzoxazole-4,7-diones and correspond to the general formula (I) defined hereafter. Given the above, these compounds are capable of being used as medicaments, in particular in the treatment and/or the prevention of the following diseases or disorders:

inhibition of tumor proliferation alone or in combination with other treatments;

inhibition of normal cell proliferation alone or in combination with other treatments;

neurodegenerative diseases such as Alzheimer's disease;

prevention of spontaneous alopecia;

prevention of alopecia induced by exogenous products;

prevention of radiation-induced alopecia;

prevention of the spontaneous or induced apoptosis of normal cells;

prevention of meiosis and/or fertilization;

prevention of the maturation of the oocytes;

all diseases/all disorders corresponding to uses reported for CDK inhibitors, and in particular non-tumorous proliferative diseases (for example: angiogenesis, psoriasis or restenosis), tumorous proliferative diseases, parasitology (proliferation of protozoans), viral infections, neurodegenerative diseases, myopathies; and/or all diseases/all disorders corresponding to clinical uses of vitamin K and its derivatives.

Moreover, the compounds of the present invention are also, because of their inhibition properties on the cdc25 phosphatases, capable of being used for inhibiting or preventing the proliferation of microorganisms, in particular yeasts. One of the advantages of these compounds is their low toxicity on healthy cells.

DETAILED DESCRIPTION OF THE INVENTION

Now, the Applicant has surprisingly discovered that the compounds corresponding to the general formula (I)

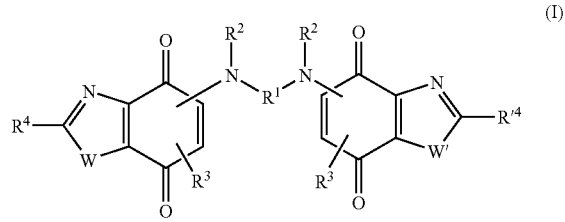

in racemic, enantiomeric form or any combination of these forms, in which:

each of W and W' represents independently O or S;

$R^1$ represents one of the —$CH_2$—$CR^6R^7$—$CH_2$—, —$(CH_2)_m$—X—$(CH_2)_n$—, —$(CH_2)_p$—[O—$(CH_2)_q]_r$—O—$(CH_2)_p$— and —$(CH_2)_s$—CO—$NR^8$—$(CH_2)_t$— radicals in which m and n are each independently an integer from 2 to 6 (preferably an integer from 2 to 4 and more preferentially an integer from 2 to 3), p and t are each independently an integer from 2 to 12 (preferably an integer from 2 to 8 and more preferentially an integer from 2 to 6), q is an integer from 2 to 4 (preferably an integer from 2 to 3), r is an integer from 0 to 4 (preferably an integer from 0 to 2), s is an integer from 1 to 12 (preferably an integer from 1 to 8 and more preferentially an integer from 1 to 6), X is chosen from the —$NR^5$—, —S—, —CO—, —$CR^6R^7$—, cycloalkyl and aryl radicals, it being understood that when X represents —S—, —CO—, —$CR^6R^7$—, cycloalkyl or aryl, m and n are equal, $R^5$ representing a hydrogen atom or an alkyl or arylalkyl radical optionally substituted 1 to 3 times by substituents chosen independently from a halogen atom and an alkyl or alkoxy radical, $R^6$ and $R^7$ each independently representing a hydrogen atom or an alkyl radical and $R^8$ representing a hydrogen atom or an alkyl or arylalkyl radical, or $R^1$ represents

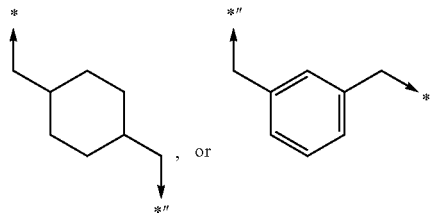

it being understood that ➤* signifies the attachment point to the general formula (I);

or also $R^1$ represents the —$(CH_2)_w$—N(Y)—$(CH_2)_w$— radical in which Y is the radical

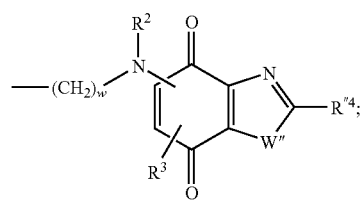

W" represents O or S and w is an integer from 2 to 3;
$R^2$ represents a hydrogen atom or an alkyl or arylalkyl radical;
$R^3$ represents a hydrogen atom or a halogen atom;
each of $R^4$, $R'^4$ and $R''^4$ represents independently a hydrogen atom, an alkyl radical, an alkoxyalkyl radical, an aryloxyalkyl radical, a phenyl radical possessing two substituents which form together a methylenedioxy or ethylene dioxy radical, a —$CH_2$—$NR^9R^{10}$ radical, a -CO—$NR^{14}R^{15}$ radical, or also a carbocyclic aryl or carbocyclic arylalkyl radical optionally substituted 1 to 4 times by substituents chosen independently from a halogen atom and an alkyl, haloalkyl, alkoxy, haloalkoxy or aryl, radical
or $R^4$ represents the radical

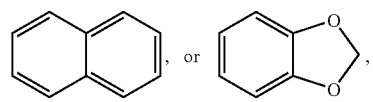

$R^9$ representing independently each time that it occurs an alkyl radical and $R^{10}$ representing independently each time that it occurs a hydrogen atom or an alkyl radical, or also $R^9$ and $R^{10}$ forming together with the nitrogen atom a heterocycle with 4 to 7 members comprising 1 to 2 heteroatoms, the members necessary for completing the heterocycle being chosen independently from the —$CR^{11}R^{12}$—, —O—, —S—, and —$NR^{13}$-radicals, $R^{11}$ and $R^{12}$ representing independently each time that they occur a hydrogen to atom or an alkyl radical and $R^{13}$ representing an alkyl or arylalkyl radical, or also $R^{13}$ representing a phenyl radical optionally substituted 1 to 3 times by substituents chosen independently from a halogen atom and an alkyl or alkoxy radical, $R^{14}$ representing independently each time that it occurs an alkyl radical, a haloalkyl radical, a cycloalkyl radical, a cycloalkylalkyl radical, an alkoxylalkyl radical, one of the carbocyclic or heterocyclic aryl or carbocyclic or heterocyclic arylalkyl radicals the aryl ring of which is optionally substituted 1 to 3 times by substituents chosen independently from the group constituted by a halogen atom, an alkyl radical an alkyl radical, an alkoxy radical, a haloalkyl radical and an —$SO_2$—$NH_2$ radical, or $R^{14}$ represents a radical

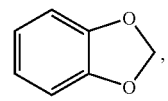

or also $R^{14}$ representing one of the —$(CH_2)_a$—[O—$(CH_2)_b]_c$—O-Alk, —$(CH_2)_d$—[O—$(CH_2)_e]_f$—$NR^{16}R^{17}$ or —$(CH_2)_g$-A radicals in which a, b and e are each independently an integer from 2 to 4, c is an integer from 1 to 4, f is an integer from 0 to 4, d is an integer from 2 to 12 (and preferably an integer from 2 to 8 and in particular an integer from 2 to 6) and g is an integer from 1 to 12 (and preferably an integer from 1 to 8 and in particular an integer from 1 to 6), Alk is an alkyl radical, $R^{16}$ is a hydrogen atom or an alkyl, alkoxycarbonyl or aralkoxycarbonyl radical, $R^{17}$ is a hydrogen atom or an alkyl radical and A is a saturated heterocycle containing 1 to 2 heteroatoms chosen independently from O, N and S and attached to the group —$(CH_2)_g$— by an N or CH member, said saturated heterocycle containing moreover from 2 to 6 additional members chosen independently from —$CHR^{18}$—, —CO—, —$NR^{19}$—, —O— and —S—, $R^{18}$ representing a hydrogen atom or an alkyl radical and $R^{19}$ representing a hydrogen atom, an alkyl radical or an alkoxycarbonyl or aralkoxycarbonyl group, and $R^{15}$ representing independently each time that it occurs a hydrogen atom or an alkyl or arylalkyl radical, $R^{15}$ also being able to represent a radical identical to $R^{14}$ when $R^{14}$ represents a carbocyclic or heterocyclic alkyl, haloalkyl, alkoxylalkyl or arylalkyl radical the aryl ring of which is optionally substituted 1 to 3 times by substituents chosen independently from the group constituted by a halogen atom, an alkyl radical, an alkoxy radical, a haloalkyl radical and an —$SO_2$—$NH_2$ radical or also $R^{14}$ and $R^{15}$ forming together with the nitrogen atom which carries them a saturated heterocycle with 4 to 7 members comprising 1 to 2 heteroatoms in total, the members necessary for completing the heterocycle being chosen independently from the —$CR^{20}R^{21}$—, —O—, —S— and —$NR^{22}$— radicals, $R^{20}$ and $R^{21}$ representing a hydrogen atom or an alkyl or arylalkyl radical and $R^{22}$ representing —$COR^{23}$ or —$SO_2R^{24}$, $R^{23}$ representing an alkyl radical, a carbocyclic aryl radical optionally substituted 1 to 3 times by substituents chosen independently from the group constituted by a halogen atom, an alkyl radical and an alkoxy radical, or also $R^{23}$ representing a heterocyclic aryl radical or a saturated heterocycle containing 5 to 7 members and 1 to 2 heteroatoms chosen independently from O, N and S (and in particular one of the piperidino, piperazino, morpholino, thiomorpholino or 2-tetrahydrofuryl radicals), $R^{24}$ representing a hydrogen atom or an alkyl radical (and preferably an alkyl radical), or finally $R^{14}$ and $R^{15}$ forming together with the nitrogen atom which carries them a heterocyclic aryl radical chosen from the radicals

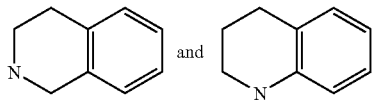

the aromatic ring of which can be substituted 1 to 3 times by substituents chosen independently from the group constituted by an alkyl radical and an alkoxy radical;

it being understood that in the case where $R^1$ represents the —$(CH_2)_w$—$N(Y)$—$(CH_2)_w$-radical, W, W' and W" are identical (in other words represent either all 0 or all S), $R^4$, $R'^4$ and $R''^4$ are identical and the nitrogen atoms adjacent to the 1,3-benzothiazole-4,7-dione or 1,3-benzoxazole-4,7-dione rings are either each attached in position 5 of the corresponding 1,3-benzothiazole-4,7-dione or 1,3-benzoxazole-4,7-dione ring or are each attached in position 6 of the corresponding 1,3-benzothiazole-4,7-dione or 1,3-benzoxazole-4,7-dione ring;

and their salts are powerful inhibitors of the Cdc25 phosphatases (and in particular of Cdc25-C phosphatase), which makes them suitable for use as anti-cancer agents.

The invention therefore relates in the first place to the compounds of general formula (I) defined previously and the salts of such compounds.

By cycloalkyl, unless otherwise specified, is meant a cycloalkyl radical containing 3 to 7 carbon atoms.

By carbocyclic or heterocyclic aryl, is meant a carbocyclic or heterocyclic system of 1 to 3 condensed rings comprising at least one aromatic ring, a system being referred to as heterocyclic when at least one of the rings which compose it comprises at least one heteroatom (O, N or S); when a carbocyclic or heterocyclic aryl radical is referred to as substituted, unless otherwise specified, it is meant that said carbocyclic or heterocyclic aryl radical is substituted 1 to 3 times, and preferably 1 to 2 times by radicals different from a hydrogen atom which, unless otherwise specified, are chosen from a halogen to atom and the alkyl or alkoxy radicals; moreover, unless otherwise specified, by aryl is exclusively meant a carbocyclic aryl.

By arylalkyl, is meant within the meaning of the present invention an -alkyl-aryl radical.

By alkyl, unless otherwise specified, is meant a linear or branched alkyl radical containing 1 to 12 carbon atoms, preferably 1 to 10 carbon atoms and more preferentially 1 to 8 carbon atoms (and in particular 1 to 6 carbon atoms).

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By haloalkyl, is meant in particular the trifluoromethyl radical. By haloalkoxy, is meant in particular the trifluoromethoxy radical. By carbocyclic aryl, is meant in particular the phenyl and naphthyl radicals. By aralkyl, is meant in particular the phenylalkyl radicals, and in particular the benzyl radical. By saturated cyclic carbon system containing 1 to 3 condensed rings chosen independently from rings with 3 to 7 members, is meant in particular the cyclopropyl, cyclobutyl, cyclohexyl and adamantyl radicals. By heterocyclic aryl or heteroaryl, is meant in particular the thienyl, furanyl, pyrrolyl, imidazolyl, thiazolyl, oxazolyl and pyridyl radicals. Finally, by halogen, is meant the fluorine, chlorine, bromine or iodine atoms.

By halogen or halogen atom is meant a chlorine, bromine, fluorine or iodine atom.

By alkoxy, unless otherwise specified, is meant a linear or branched alkoxy radical containing 1 to 6 carbon atoms (and in particular 1 to 4 carbon atoms).

By haloalkyl, is meant an alkyl radical at least one (and optionally all) of the hydrogen atoms of which is replaced by a halogen atom.

By cycloalkylalkyl, alkoxylalkyl, haloalkyl, haloalkoxy and aralkyl radicals, is meant respectively the cycloalkylalkyl, alkoxylalkyl, haloalkyl, haloalkoxy and aralkyl radicals the alkyl, cycloalkyl and aryl radicals of which have the meanings indicated previously.

When it is indicated that a radical is optionally substituted 1 to 4 times, it is preferably optionally substituted 1 to 3 times, more preferentially optionally substituted 1 to 2 times and yet more preferentially optionally substituted once.

By salt of a compound, is meant the addition salts of said compound with an organic or inorganic acid or, if appropriate, with a base, and in particular the pharmaceutically acceptable salts of said compound.

By pharmaceutically acceptable salt, is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In certain cases, the compounds according to the present invention can comprise asymmetrical carbon atoms. As a result, the compounds according to the present invention have two possible enantiomeric forms, i.e. the "R" and "S" configurations. The present invention includes the two enantiomeric forms and all combinations of these forms, including the "RS" racemic mixtures. In an effort to simplify matters, when no specific configuration is indicated in the structural formulae, it should be understood that the two enantiomeric forms and their mixtures are represented.

According to a general variant of the invention, the compounds of general formula (I) or their salts are such that $R^1$ does not represent a —$(CH_2)_w$—$N(Y)$—$(CH_2)_w$— radical, W and W' being identical and $R^4$ and $R'^4$ being identical; for the remainder of this disclosure, the compounds of general formula (I) such that $R^1$ does not represent a —$(CH_2)_w$—N(Y)—$(CH_2)_w$— radical, W and W' being identical and $R^4$ and $R'^4$ being identical are called "compounds of general formula $(I)_D$".

A particular aspect of this general variant of the invention relates to the compounds of general formula $(I)_D$ in which each of W and W' represents S, which are designated in the remainder of this disclosure "compounds of general formula $(I)_{DS}$", as well as the salts of these compounds. The invention relates to in particular the compounds of general formula $(I)_{DS}$ in which the —$N(R^2)$—$R^1$—$N(R^2)$— bond chain will be positioned so that it connects positions 5 of die 1,3-benzothiazole-4,7-dione units, namely
the compounds of general sub-formula $(I)_{DS5}$

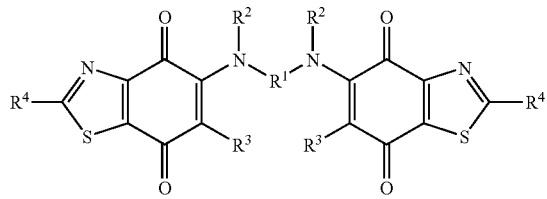

$(I)_{DS5}$ in which $R^1$ has the same meaning as in the general formula $(I)_D$ and $R^2$, $R^3$ and $R^4$ have the same meaning as in the general formula (I), as well as the salts of these compounds. It also relates to the compounds of general formula $(I)_{DS}$ in which the —$N(R^2)$—$R^1$—$N(R^2)$— bond chain will be positioned so that it connects positions 6 of the units 1,3-benzothiazole-4,7-dione, namely the compounds of general sub-formula $(I)_{DS6}$

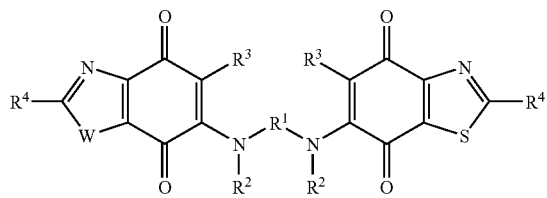

$(I)_{DS6}$ in which $R^1$ has the same meaning as in the general formula (I), and $R^2$, $R^3$ and $R^4$ have to the same meaning as in the general formula (I), as well as the salts of these compounds.

Another particular aspect of this general variant of the invention relates to the compounds of general formula $(I)_D$ in which each of W and W' represents O, which are designated in the remainder of this disclosure "compounds of general formula $(I)_{DO}$", as well as the salts of these compounds. The invention relates in particular to the compounds of general formula $(I)_{DO}$ in which the —$N(R^2)$—$R^1$—$N(R^2)$— bond chain will be positioned so that it connects positions 5 of the 1,3-benzoxazole-4,7-dione units, namely the compounds of general sub-formula $(I)_{DO5}$

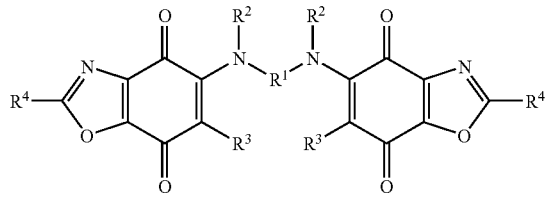

$(I)_{DO5}$ in which $R^1$ has the same meaning as in the general formula $(I)_D$ and $R^2$, $R^3$ and $R^4$ have the same meaning as in the general formula (I), as well as the salts of these compounds. It also relates to the compounds of general formula $(I)_{DO}$ in which the —$N(R^2)$—$R^1$—$N(R^2)$— bond chain will be positioned so that it connects positions 6 of the 1,3-benzoxazole-4,7-dione units, namely the compounds of general sub-formula $(I)_{DO6}$

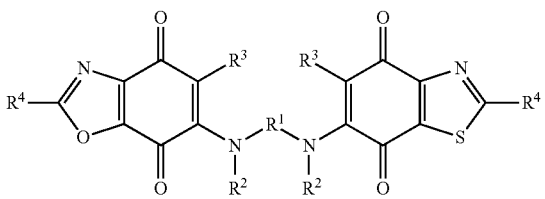

$(I)_{DO6}$ in which $R^1$ has the same meaning as in the general formula $(I)_D$ and $R^2$, $R^3$ and $R^4$ have the same meaning as in the general formula (I), as well as the salts of these compounds.

According to another general variant of the invention, the compounds of general formula (I) or their salts are such that $R^1$ represents a —$(CH_2)_w$—$N(Y)$—$(CH_2)_w$— radical; for to the remainder of this disclosure, the compounds of general formula (I) such that $R^1$ represents a —$(CH_2)_w$—$N(Y)$—$(CH_2)_w$— radical are called "compounds of general formula $(I)_T$".

A particular aspect of this general variant of the invention relates to the compounds of general formula $(I)_T$ in which each of W, W' and W" represents S, which are designated in the remainder of this disclosure "compounds of general formula $(I)_{TS}$", as well as the salts of these compounds. The invention relates to in particular the compounds of general formula $(I)_{TS}$ in which the —$N(R^2)$—$R^1$—$N(R^2)$— bond chain will be positioned so that it connects positions 5 of the 1,3-benzothiazole-4,7-dione units, namely the compounds of general sub-formula $(I)_{TS5}$

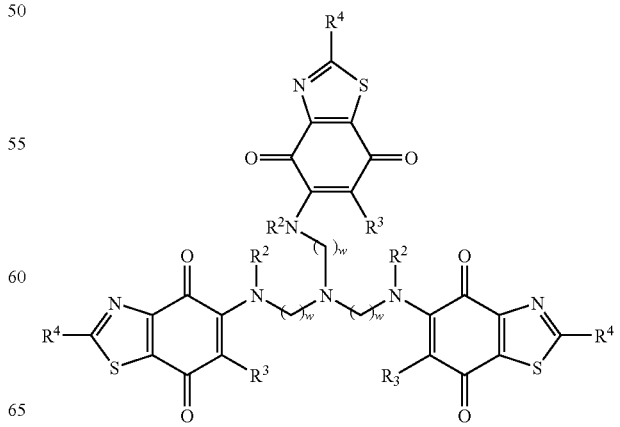

$(I)_{TS5}$ in which w, $R^2$, $R^3$ and $R^4$ have the same meaning as in the general formula (I), as well as the salts of these compounds. It also relates to the compounds of general formula $(I)_{TS}$ in which the $-N(R^2)-R^1-N(R^2)-$ bond chain will be positioned so that it connects positions 6 of the 1,3-benzothiazole-4,7-dione units, namely the compounds of general sub-formula $(I)_{TS6}$

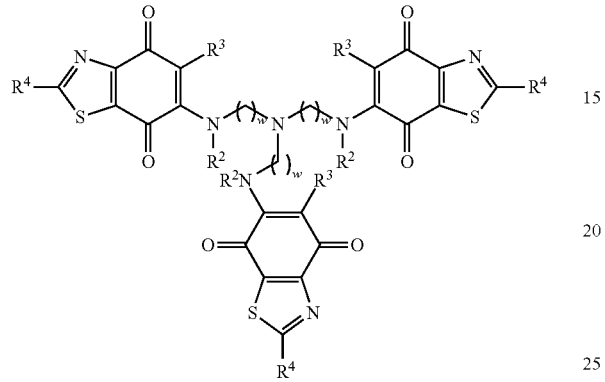

$(I)_{TS6}$ in which $R^1$ has the same meaning as in the general formula $(I)_T$ and $R^2$, $R^3$ and $R^4$ have the same meaning as in the general formula (I), as well as the salts of these compounds.

Another particular aspect of this general variant of the invention relates to the compounds of general formula $(I)_T$ in which each of W, W' and W" represents O, which are designated in the remainder of this disclosure "compounds of general formula $(I)_{TO}$", as well as the salts of these compounds. The invention relates to in particular the compounds of general formula $(I)_{TO}$ in which the $-N(R^2)-R^1-N(R^2)-$ bond chain will be positioned so that it connects positions 5 of the 1,3-benzoxazole-4,7-dione units, namely the compounds of general sub-formula $(I)_{TO5}$

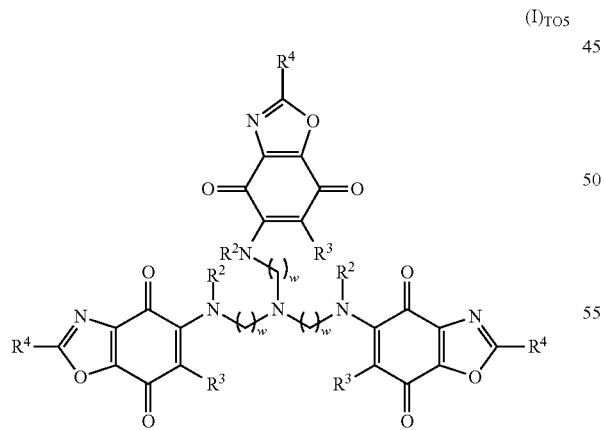

$(I)_{TO5}$ in which w, $R^2$, $R^3$ and $R^4$ have the same meaning as in the general formula (I), as well as the salts of these compounds. It also relates to the compounds of general formula $I_{DO}$ in which the $-N(R^2)-R^1-N(R^2)-$ bond chain will be positioned so that it connects positions 6 of the 1,3-benzoxazole-4,7-dione units, namely the compounds of general sub-formula $(I)_{TO6}$

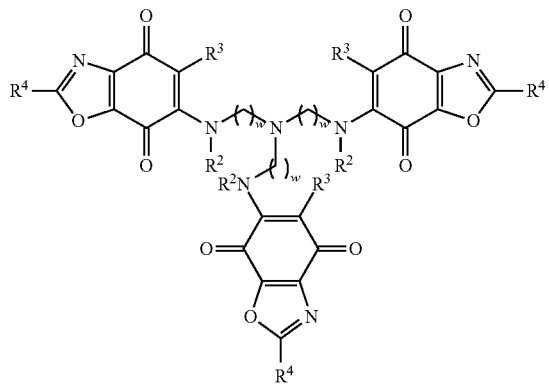

$(I)_{TO6}$ in which w, $R^2$, $R^3$ and $R^4$ have the same meaning as in the general formula (I), as well as the salts of these compounds.

According to yet another general variant of the invention, the compounds of general formula (I) or their salts are such that $R^1$ does not represent a $-(CH_2)_w-N(Y)-(CH_2)_w-$ radical and one of W and W' represents O whilst the other represents S and/or $R^4$ and $R'^4$ are different; for the remainder of this disclosure, the compounds of general formula (I) are such that $R^1$ does not represent a $-(CH_2)_w-N(Y)-(CH_2)_w-$ radical and one of W and W' represents O whilst the other represents S and/or $R^4$ and $R'^4$ are different are called "compounds of general formula $(I)_{DM}$".

Preferably, the compounds of general formula (I) or their salts are such that they have at least one of the following characteristics:

$R^1$ representing one of the $-CH_2-CR^6-R^7-CH2-$, $-(CH_2)_m-X-(CH_2)_n-$, $-(CH_2)_p-[O-(CH_2)_q]_r-O-(CH_2)_p-$, $-(CH_2)_s-CO-NR^8-(CH_2)_t-$ radicals or $R^1$ representing the $-(CH_2)_w-N(Y)-(CH_2)_w-$, radical;

$R^2$ representing a hydrogen atom or the methyl, ethyl or benzyl radical;

$R^3$ representing a hydrogen atom or a halogen atom;

each of $R^4$, $R'^4$ and $R'''^4$ representing independently a hydrogen atom, an alkyl, $-CO-NR^{14}R^{15}$ radical or also a carbocyclic aryl or carbocyclic arylalkyl radical optionally substituted 1 to 4 times by substituents chosen independently from a halogen atom and an alkyl, haloalkyl, alkoxy, haloalkoxy or aryl radical.

More preferentially, the compounds of general formula (I) or their salts are such that they have at least one of the following characteristics:

$R^1$ representing one of the $-(CH_2)_m-X-(CH_2)_n-$ radicals, or $R^1$ representing the $-(CH_2)_w-N(Y)-(CH_2)_w-$ radical (w representing preferably 2);

$R^2$ representing a hydrogen atom or the methyl radical;

each of $R^4$, $R'^4$ and $R'''^4$ representing independently a hydrogen atom, an alkyl, $-CO-NR^{14}R^{15}$ radical or also a carbocyclic aryl or carbocyclic arylalkyl radical optionally substituted 1 to 4 times by substituents chosen independently from a halogen atom (the fluorine atoms being preferred from the halogen substituents) and an radical, trifluoromethyl, alkoxy, trifluoromethoxy or phenyl alkyl.

Still more preferentially, the compounds of general formula (I) or their salts are such that they have at least one of the following characteristics:

$R^1$ representing $-(CH_2)_m-X-(CH_2)_n-$;

$R^2$ representing a hydrogen atom.

Still more preferentially, the compounds of general formula (I) or their salts are such that:

R¹ representing one of the —CH₂—CR⁶R⁷—CH₂—, —(CH₂)$_m$—X—(CH₂)$_n$—, —(CH₂)$_p$—[O—(CH₂)$_q$]$_r$—O—(CH₂)$_p$—, —(CH₂)$_s$—CO—NR⁸—(CH₂)$_t$— radicals or R¹ representing the —(CH₂)$_w$—N(Y)—(CH₂)$_w$— radical;

Still more preferentially, the compounds of general formula (I) or their salts are such that:

R¹ representing —(CH₂)$_m$—X—(CH₂)$_n$—.

Moreover, the compounds of general formula (I) (or their salts) are generally preferred such that they have at least one of the following characteristics:

X represents —NR⁵— or —CR⁶R⁷—;

R⁸ represents a hydrogen atom or a methyl radical;

R¹⁴ represents independently each time that it occurs an alkyl radical, a cycloalkyl radical, a cycloalkylalkyl radical, an alkoxylalkyl radical, one of the carbocyclic aryl or carbocyclic or heterocyclic arylalkyl radicals the aryl ring of which is optionally substituted 1 to 3 times by substituents chosen independently from the group constituted by a halogen atom, an alkyl radical and an alkoxy radical, or also R¹⁴ represents one of the —(CH₂)$_a$—[O—(CH₂)$_b$]$_c$—O-Alk, —(CH₂)$_d$—[O—(CH₂)$_e$]$_f$—NR¹⁶R¹⁷ or —(CH₂)$_g$-A radicals in which a, b and e are each independently 2 or 3, c is an integer from 1 to 3, f is an integer from 0 to 3, d is an integer from 2 to 6 and g is an integer from 1 to 6, Alk is an alkyl radical, R¹⁶ is a hydrogen atom or an alkoxycarbonyl radical, R¹⁷ is a hydrogen atom or a methyl radical and A is a saturated heterocycle containing 1 to 2 heteroatoms chosen independently from O, N and S and attached to the —(CH₂)$_g$— group by an N or CH member, said saturated heterocycle containing moreover from 2 to 6 additional members chosen independently from CHR¹⁸—, —CO—, —NR¹⁹—, —O— and —S—, R¹⁸ representing a hydrogen atom or a methyl radical and R¹⁹ representing a hydrogen atom, an alkyl radical or an alkoxycarbonyl group, or also R¹⁴ represents a radical

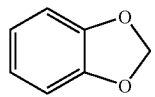

and R¹⁵ represents independently each time that it occurs a hydrogen atom or an alkyl or arylalkyl radical, R¹⁵ also being able to represent a radical identical to R¹⁴ when R¹⁴ represents a carbocyclic or heterocyclic alkyl, alkoxylalkyl or arylalkyl radical, the aryl ring of which is optionally substituted 1 to 3 times by substituents chosen independently from the group constituted by a halogen atom, an alkyl radical and an alkoxy radical, or also R¹⁴ and R¹⁵ form together with the nitrogen atom which carries them a saturated heterocycle with 4 to 7 members comprising 1 to 2 heteroatoms in total, the members necessary for completing the heterocycle being chosen independently from the —CR²⁰R²¹—, —O—, —S— and —NR²²— radicals, R²⁰ and R²¹ representing a hydrogen atom or an alkyl or arylalkyl radical and R²² representing —COR²³ or —SO₂R²⁴, R²³ representing an alkyl radical, a carbocyclic aryl radical optionally substituted 1 to 3 times by substituents chosen independently from the group constituted by a halogen atom, an alkyl radical and an alkoxy radical, or also R²³ representing a heterocyclic aryl radical or a saturated heterocycle chosen from the piperidino, piperazino, morpholino, thiomorpholino and 2-tetrahydrofuryl radicals, R²⁴ representing a hydrogen atom or an alkyl radical;

or also R¹⁴ and R¹⁵ forming together with the nitrogen atom which carries them a heterocyclic aryl radical of the type

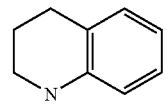

the aromatic ring of which can be substituted 1 to 3 times by substituents chosen independently from the group constituted by an alkyl radical and an alkoxy radical. Generally, the compounds of general formula (I) (or their salts) are yet more preferred such that they have at least one of the following characteristics:

X represents —NR⁵— in which R⁵ represents a methyl or arylalkyl radical optionally substituted by an alkoxy group (and in particular methoxy);

R⁸ represents a hydrogen atom;

R¹⁴ represents independently each time that it occurs an alkyl radical, a cycloalkyl radical, a cycloalkylalkyl radical, an alkoxylalkyl radical, one of the carbocyclic aryl or carbocyclic or heterocyclic arylalkyl radicals the aryl ring of which is optionally substituted 1 to 3 times by substituents chosen independently from the group constituted by a halogen atom, an alkyl radical and an alkoxy radical, or also R¹⁴ represents one of the —(CH₂)$_d$—[O—(CH₂)$_e$]$_f$—NR¹⁶R¹⁷ or —(CH₂)$_g$-A radicals in which c is 2 or 3, f is an integer from 0 to 3, d is an integer from 2 to 6 and g is an integer from 1 to 6, R¹⁶ is a hydrogen atom or an alkoxycarbonyl radical (and in particular tert-butoxycarbonyl), R¹⁷ is a hydrogen atom and A is a saturated heterocycle containing 1 to 2 heteroatoms chosen independently from O, N and S and attached to the group —(CH₂)$_g$— by an N or CH member, said saturated heterocycle containing moreover from 2 to 6 additional members chosen independently from —CHR¹⁸—, —CO—, —NR¹⁹, —O— and —S—, R¹⁸ representing a hydrogen atom or a methyl radical and R¹⁹ representing a hydrogen atom, an alkyl radical or an alkoxycarbonyl group (and in particular tert-butoxycarbonyl), or also R¹⁴ represents a radical

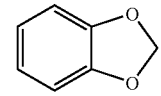

and R¹⁵ represents independently each time that it occurs a hydrogen atom, R¹⁵ also being able to represent a radical identical to R¹⁴ when R¹⁴ represents a carbocyclic or heterocyclic alkyl, alkoxylalkyl or arylalkyl radical the aryl ring of which is optionally substituted 1 to 3 times by substituents chosen independently from the group constituted by a halogen atom, an alkyl radical and an alkoxy radical, or also R¹⁴ and R¹⁵ form together with the nitrogen atom which carries them a saturated heterocycle with 4 to 7 members comprising 1 to 2 heteroatoms in total, the members necessary for completing the heterocycle being chosen independently from the —CR$^{20}$R$^{21}$—, —O—, —S— and —NR$^{22}$— radicals, R$^{20}$ and R$^{21}$ representing a hydrogen atom or an alkyl radical and R$^{22}$ representing COR$^{23}$ or —SO$_2$R$^{24}$, R$^{23}$ representing an alkyl radical, a carbocyclic aryl radical optionally substituted 1 to 3 times by substituents chosen independently from the group constituted by a halogen atom, an alkyl radical and an alkoxy radical, or also R$^{23}$ representing a heterocyclic aryl radical or a saturated heterocycle chosen from the piperidino, piperazino, morpholino, thiomorpholino and 2-tetrahydrofuryl radicals, R$^{24}$ representing a hydrogen atom or an alkyl radical;

or also R$^{14}$ and R$^{15}$ forming together with the nitrogen atom which carries them a heterocyclic aryl radical of the type

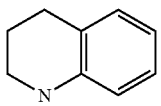

the aromatic ring of which can be substituted 1 to 3 times by substituents chosen independently from the group constituted by an alkyl radical and an alkoxy radical, in particular methoxy.

Generally, the compounds of general formula (I) (or their salts) are yet more preferred such that they have at least one of the following characteristics:

X represents —NR$^5$— in which R$^5$ represents a methyl radical;

R$^{14}$ represents independently each time that it occurs an alkyl radical, a cycloalkyl radical, a cycloalkylalkyl radical, an alkoxyalkyl radical, one of the carbocyclic aryl or carbocyclic or heterocyclic arylalkyl radicals the aryl ring of which is optionally substituted 1 to 3 times by substituents chosen independently from the group constituted by a halogen atom, an alkyl radical and an alkoxy radical, or also R$^{14}$ represents one of the —(CH$_2$)$_d$—[O—(CH$_2$)$_e$]$_f$—NR$^{16}$R$^{17}$ or —(CH$_2$)$_g$-A radicals in which e is 2 or 3, f is an integer from 0 to 3, d is an integer from 2 to 6 and g is an integer from 1 to 6, R$^{16}$ is a hydrogen atom or an alkoxycarbonyl radical (and in particular tert-butoxycarbonyl), R$^{17}$ is a hydrogen atom and A is a saturated heterocycle containing 1 to 2 heteroatoms chosen independently from O, N and S and attached to the group —(CH$_2$)$_g$— by an N or CH member, said saturated heterocycle containing moreover from 2 to 6 additional members chosen independently from CHR$^{18}$—, —CO—, —NR$^{19}$—, —O— and —S—, R$^{18}$ representing a hydrogen atom or a methyl radical and R$^{19}$ representing a hydrogen atom, an alkyl radical or an alkoxycarbonyl group (and in particular tert-butoxycarbonyl), or also R$^{14}$ represents a radical

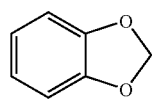

and R$^{15}$ represents independently each time that it occurs a hydrogen atom, or also R$^{14}$ and R$^{15}$ form together with the nitrogen atom which carries them a saturated heterocycle with 4 to 7 members comprising 1 to 2 heteroatoms in total, the members necessary for completing the heterocycle being chosen independently from the —CR$^{20}$R$^{21}$—, —O—, —S— and —NR$^{22}$— radicals, R$^{20}$ and R$^{21}$ representing a hydrogen atom or a methyl radical and R$^{22}$ representing COR$^{23}$ or —SO$_2$R$^{24}$, R$^{23}$ representing an alkyl radical, a carbocyclic aryl radical optionally substituted 1 to 3 times by substituents chosen independently from the group constituted by a halogen atom, an alkyl radical and an alkoxy radical, or also R$^{23}$ representing a heterocyclic aryl radical or a saturated heterocycle chosen from the piperidino, piperazino, morpholino and 2-tetrahydrofuryl radicals, R$^{24}$ representing a hydrogen atom or an alkyl radical (and in particular an alkyl radical, in particular methyl);

or also R$^{14}$ and R$^{15}$ forming together with the nitrogen atom which carries them a heterocyclic aryl radical of the type

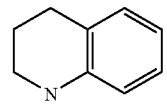

the aromatic ring of which can be substituted by a methoxy radical.

Among the compounds of general formula (I), the following compounds described in the examples are in particular preferred:

-5.5'-[(methylimino)bis(propane-3,1-diylimino)]bis(2-methyl-1,3-benzothiazole-4,7-dione);
-5.5'-[(methylimino)bis(ethane-2,1-diylimino)]bis(2-methyl-1,3-benzothiazole-4,7-dione);
-5.5'-[oxybis(ethane-2,1-diylimino)]bis(2-methyl-1,3-benzothiazole-4,7-dione);
-5.5'-(pentane-1,5-diyldiimino)bis(2-methyl-1,3-benzothiazole-4,7-dione);
-6.6'-[(methylimino)bis(propane-3,1-diylimino)]bis(2-methyl-1,3-benzothiazole-4,7-dione);
-6.6'-[(methylimino)bis(ethane-2,1-diylimino)]bis(2-methyl-1,3-benzothiazole-4,7-dione);
-5.5'-[(methylimino)bis(propane-3,1-diylimino)]bis{4,7-dioxo-N-[3-(2-oxopyrrolidin-1-yl)propyl]-4,7-dihydro-1,3-benzothiazole-2-carboxamide};
-6.6'-[(methylimino)bis(propane-3,1-diylimino)]bis[2-(2,5-difluorophenyl)-1,3-benzoxazole-4,7-dione];
-6.6'-[(methylimino)bis(propane-3,1-diylimino)]bis[2-(3,5-dibromophenyl)-1,3-benzoxazole-4,7-dione];
-6.6'-[(methylimino)bis(propane-3,1-diylimino)]bis[2-(2-chloro-6-fluorobenzyl)-1,3-benzoxazole-4,7-dione];
-6.6'-[(methylimino)bis(propane-3,1-diylimino)]bis[2-(3-bromophenyl)-1,3-benzoxazole-4,7-dione];
-6.6'-[(methylimino)bis(propane-3,1-diylimino)]bis[2-(4-bromophenyl)-1,3-benzoxazole-4,7-dione];
-6.6'-[(methylimino)bis(propane-3,1-diylimino)]bis[2-(3,5-difluorophenyl)-1,3-benzoxazole-4,7-dione];
-6.6'-[(methylimino)bis(propane-3,1-diylimino)]bis[2-(3-chlorophenyl)-1,3-benzoxazole-4,7-dione];
-6.6'-[(methylimino)bis(propane-3,1-diylimino)]bis[2-(4-fluorophenyl)-1,3-benzoxazole-4,7-dione];
-6.6'-[(methylimino)bis(propane-3,1-diylimino)]bis[2-(4-bromo-3-methylphenyl)-1,3-benzoxazole-4,7-dione];
-5.5'-[(methylimino)bis(propane-3,1-diylimino)]bis(6-bromo-2-methyl-1,3-benzothiazole-4,7-dione);

-5,5',5''-[nitrilotris(propane-3,1-diylimino)]tris(2-methyl-1,3-benzothiazole-4,7-dione);
-5,5'-(2,2-dimethylpropane-1,3-diyldiimino)bis(2-methyl-1,3-benzothiazole-4,7-dione);
-5,5'-[cyclohexane-1,4-diylbis(methyleneimino)]bis(2-methyl-1,3-benzothiazole-4,7-dione);
-5,5'-[1,3-phenylenebis(methyleneimino)]bis(2-methyl-1,3-benzothiazole-4,7-dione);
-5,5'-[ethane-1,2-diylbis(oxypropane-3,1-diylimino)]bis(2-methyl-1,3-benzothiazole-4,7-dione);
-6,6'-{(methylimino)bis[propane-3,1-diyl(methylimino)]}bis[2-(2,5-difluorophenyl)-1,3-benzoxazole-4,7-dione];
—$N^3$-[2-(2,5-difluorophenyl)-4,7-dioxo-4,7-dihydro-1,3-benzoxazol-6-yl]-$N^1$-(3-{[2-(2,5-difluorophenyl)-4,7-dioxo-4,7-dihydro-1,3-benzoxazol-6-yl]amino}propyl)-β-alaninamide;
-5,5'-[(methylimino)bis(propane-3,1-diylimino)]bis(1,3-benzothiazole-4,7-dione);
-5,5'-[(methylimino)bis(propane-3,1-diylimino)]bis[2-(morpholin-4-ylcarbonyl)-1,3-benzothiazole-4,7-dione];
-5,5'-[(methylimino)bis(propane-3,1-diylimino)]bis(2-{[4-(morpholin-4-ylcarbonyl)piperazin-1-yl]carbonyl}-1,3-benzothiazole-4,7-dione);
-5,5'-[(methylimino)bis(propane-3,1-diylimino)]bis(2-{[4-(tetrahydrofuran-2-ylcarbonyl)piperazin-1-yl]carbonyl}-1,3-benzothiazole-4,7-dione);
-5,5'-[(methylimino)bis(propane-3,1-diylimino)]bis(2-{[4-(methylsulphonyl)piperazin-1-yl]carbonyl}-1,3-benzothiazole-4,7-dione);
-5,5'-[(methylimino)bis(propane-3,1-diylimino)]bis[N-(4-methoxyphenyl)-4,7-dioxo-4,7-dihydro-1,3-benzothiazole-2-carboxamide];
-6,6'-[(methylimino)bis(propane-3,1-diylimino)]bis[2-(pyrrolidin-1-ylcarbonyl)-1,3-benzothiazole-4,7-dione];
-5,5'-[(methylimino)bis(propane-3,1-diylimino)]bis[N-(4-fluorophenyl)-4,7-dioxo-4,7-dihydro-1,3-benzothiazole-2-carboxamide];
-5,5'-[(methylimino)bis(propane-3,1-diylimino)]bis[N-(4-methoxybenzyl)-4,7-dioxo-4,7-dihydro-1,3-benzothiazole-2-carboxamide];
-5,5'-[(methylimino)bis(propane-3,1-diylimino)]bis{2-[(6-methoxy-3,4-dihydroquinolin-1(2H)-yl)carbonyl]-1,3-benzothiazole-4,7-dione};
-5,5'-[(methylimino)bis(propane-3,1-diylimino)]bis(N-cyclohexyl-4,7-dioxo-4,7-dihydro-1,3-benzothiazole-2-carboxamide);
-5,5'-[(methylimino)bis(propane-3,1-diylimino)]bis(2-{[4-(4-methoxybenzoyl)piperazin-1-yl]carbonyl}-1,3-benzothiazole-4,7-dione);
-5,5'-[(methylimino)bis(propane-3,1-diylimino)]bis(2-{[4-(2-furoyl)piperazin-1-yl]carbonyl}-1,3-benzothiazole-4,7-dione);
-6,6'-[(methylimino)bis(propane-3,1-diylimino)]bis[2-(2-naphthyl)-1,3-benzothiazole-4,7-dione];
-6,6'-[(methylimino)bis(propane-3,1-diylimino)]bis[2-(1,3-benzodioxol-5-yl)-1,3-benzothiazole-4,7-dione];
-6,6'-[(methylimino)bis(propane-3,1-diylimino)]bis[2-(4-ethylphenyl)-1,3-benzoxazole-4,7-dione];
—N-(4-methoxyphenyl)-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide;
-5-{[3-(methyl{3-[(2-methyl-4,7-dioxo-4,7-dihydro-1,3-benzothiazol-6-yl)amino]propyl}amino)propyl]amino}-2-{[4-(tetrahydrofuran-2-ylcarbonyl)piperazin-1-yl]carbonyl}-1,3-benzothiazole-4,7-dione;
—N-ethyl-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide;
-5-({3-[(3-{[(4,7-dioxo-2-(pyrrolidin-1-ylcarbonyl)-4,7-dihydro-1,3-benzothiazol-6-yl]amino}propyl)(methyl)amino]propyl}amino)-2-methyl-1,3-benzothiazole-4,7-dione;
—N-(4-methoxybenzyl)-5-{[3-(methyl{3-[(2-methyl-4,7-dioxo-4,7-dihydro-1,3-benzothiazol-3-yl)amino]propyl}amino)propyl]amino}-4,7-dioxo-4,7-dihydro-1,3-benzothiazole-2-carboxamide;
—N-1,3-benzodioxol-5-yl-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide;
-2-[(6-methoxy-3,4-dihydroquinolin-1(2H)-yl)carbonyl]-5-{[3-(methyl{3-[(2-methyl-4,7-dioxo-4,7-dihydro-1,3-benzothiazol-5-yl)amino]propyl}amino)propyl]amino}-1,3-benzothiazole-4,7-dione;
-2-{[4-(4-methoxybenzoyl)piperazin-1-yl]carbonyl}-5-{[3-(methyl{3-[(2-methyl-4,7-dioxo-4,7-dihydro-1,3-benzothiazol-5-yl)amino]propyl}amino)propyl]amino}-1,3-benzothiazole-4,7-dione;
-5-({3-[(3-{[2-(4-methoxyphenyl)-4,7-dioxo-4,7-dihydro-1,3-benzothiazol-6-yl]amino}propyl)(methyl)amino]propyl}amino)-2-methyl-1,3-benzothiazole-4,7-dione;
-5-({3-[{3-[(4,7-dioxo-4,7-dihydro-1,3-benzothiazol-5-yl)amino]propyl}(methyl)amino]propyl}amino)-2-methyl-1,3-benzothiazole-4,7-dione;
-2-(2,5-difluorophenyl)-6-{[3-(methyl{3-[(2-methyl-4,7-dioxo-4,7-dihydro-1,3-benzothiazol-5-yl)amino]propyl}amino)propyl]amino}-1,3-benzoxazole-4,7-dione;
-2-(4-ethylphenyl)-6-{[3-(methyl{3-[(2-methyl-4,7-dioxo-4,7-dihydro-1,3-benzothiazol-5-yl)amino]propyl}amino)propyl]amino}-1,3-benzoxazole-4,7-dione;
-2-(2,5-difluorophenyl)-6-{[3-(methyl{3-[(2-methyl-4,7-dioxo-4,7-dihydro-1,3-benzothiazol-6-yl)amino]propyl}amino)propyl]amino}-1,3-benzoxazole-4,7-dione;
-5,5'-[[(4-methoxybenzyl)imino]bis(propane-3,1-diylimino)]bis(2-methyl-1,3-benzothiazole-4,7-dione);
-5,5'-[(methylimino)bis(butane-4,1-diylimino)]bis(2-methyl-1,3-benzothiazole-4,7-dione);
-2-methyl-5-{[3-(methyl{4-[(2-methyl-4,7-dioxo-4,7-dihydro-1,3-benzothiazol-5-yl)amino]butyl}amino)propyl]amino}-1,3-benzothiazole-4,7-dione;
and the salts of these compounds.

The invention also relates to, as medicaments, the compounds of general formula (I) mentioned above, or their pharmaceutically acceptable salts.

A subject of the invention is also the pharmaceutical compositions comprising, as active ingredient, a compound of general formula (I) or a pharmaceutically acceptable salt of such a compound, with at least one pharmaceutically acceptable excipient.

Another subject of the invention is the use of the compounds of general formula (I) or their pharmaceutically acceptable salts for preparing a medicament intended to treat a disease/a disorder chosen from the following diseases/the following disorders: tumorous proliferative diseases (and in particular cancer), non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases or allergies.

Quite particularly, the compounds of general formula (I) or their pharmaceutically acceptable salts can be used for preparing a medicament intended to treat cancer, and in particular breast cancer, lymphomas, cancers of the neck or head, lung cancer, cancer of the colon, prostate cancer or cancer of the pancreas.

The invention relates moreover to a treatment method for one of the diseases/one of the disorders mentioned, said method comprising the administration to the patient suffering from said disease/said disorder of a therapeutically effective quantity of a compound of general formula (I) or a pharmaceutically acceptable salt of such a compound.

The preferences mentioned for the compounds of general formula (I) and their salts are of course applicable mutatis mutandis to the compounds of general formulae $(I)_D$, $(I)_{DS}$, $(I)_{DS5}$, $(I)_{DS6}$, $(I)_{DO}$, $(I)_{DO5}$, $(I)_{DO6}$, $(I)_T$, $(I)_{TS}$, $(I)_{TS5}$, $(I)_{TS6}$, $(I)_{TO}$, $(I)_{TO5}$, $(I)_{TO6}$ or $(I)_{DM}$, as well as to the medicaments, pharmaceutical compositions and uses according to the invention relating to said compounds and their pharmaceutically acceptable salts.

The pharmaceutical compositions containing a compound of the invention can be presented in solid form, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water.

The administration of a medicament according to the invention can be carried out by topical, oral, parenteral route, by intramuscular injection, etc.

The administration dose envisaged for a medicament according to the invention is comprised between 0.1 mg to 10 g depending on the type of active ingredient used.

According to the invention, the compounds of general formula (I) can be prepared by the processes described hereafter.
Preparation of the Compounds of General Formula (I)

The preparation processes hereafter are given by way of illustration and are non limitative.
General Methods:

i) Compounds of General Formula $(I)_D$ in which R5 is Different from Arylalkyl:

The compounds of general formula (I), in which $R^3$ represents a hydrogen atom, W, $R^2$ and $R^4$ are as defined previously and $R^1$ is as defined previously, but where $R^5$ does not represent an arylalkyl radical, can be prepared according to the procedure summarized in Diagram 1 hereafter.

Diagram 1

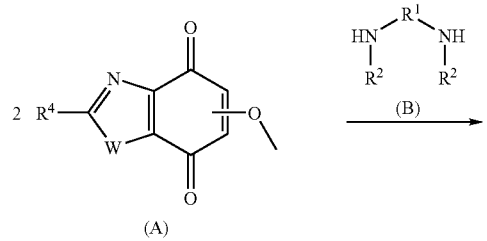

-continued

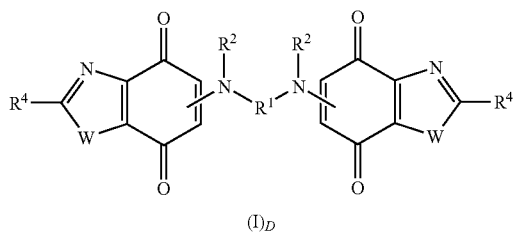

$(I)_D$

According to this method, the compounds of general formula (I), in which $R^1$, $R^2$, $R^4$ and W are as described above, are obtained by treatment of the compounds of general formula (A), with amines of general formula $R^2HNR^1NHR^2$ (hereafter the amines of general formula (B)) in a protic solvent such as methanol or ethanol, at a temperature preferably comprised between 20° C. and 80° C. and optionally in the presence of a base such as, for example, diisopropylethylamine (Yasuyuki Kita et al., *J. Org. Chem.* (1996), 61, 223-227).

ii) Compounds of General Formula $(I)_T$:

The compounds of general formula $(I)_T$ in which $R^3$ represents a hydrogen atom and W, $R^1$, $R^2$ and $R^4$ are as defined previously can be prepared according to the procedure summarized in Diagram 1a hereafter. The reaction conditions are similar to those used for the synthesis represented in Diagram 1.

Diagram 1a

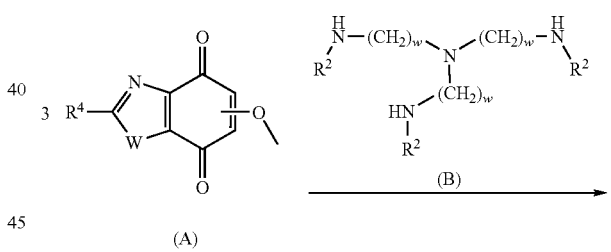

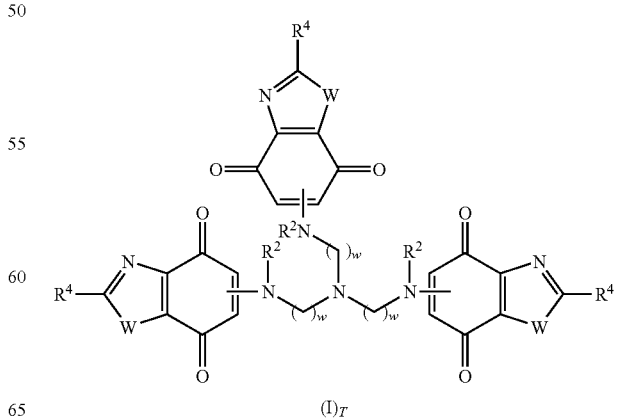

$(I)_T$ iii) Compounds of General Formula $(I)_D$ or $(I)_T$ in which $R^3$ is a Halogen Atom:

Generally, the compounds of general formula (I) in which $R^3$ is a halogen atom (Hal) can be obtained, Diagram 1b (in which only the preparation of the halogenated compounds of general formula $(I)_D$ is represented), from the compounds of general formula (I) in which $R^3$ represents a hydrogen atom, for example by the action of N-chlorosuccinimide or N-bromosuccinimide in an aprotic solvent such as dichloromethane or tetrahydrofuran (Paquette and Farley, *J. Org. Chem.* (1967), 32, to 2725-2731), by the action of an aqueous solution of sodium hypochlorite (Javel water) in a solvent such as acetic acid (Jagadeesh et al., *Synth Commun.* (1998), 28, 3827-3833), by the action of Cu(II) (in a $CuCl_2/HgCl_2$ mixture) in the presence of a catalytic quantity of iodine in a solvent such as warm acetic acid (Thapliyal, *Synth. Commun.* (1998), 28, 1123-1126), by the action of a agent such as benzyltrimethylammonium dichloroiodate in the presence of $NaHCO_3$ in a solvent such as a dichloromethane/methanol mixture (Kordik and Reitz, *J. Org. Chem.* (1996), 61, 5644-5645), or also by use of chlorine, bromine or iodine in a solvent such as dichloromethane (J. Renault, S. Giorgi-Renault et al., *J. Med. Chem.* (1983), 26, 1715-1719).

Diagram 1b

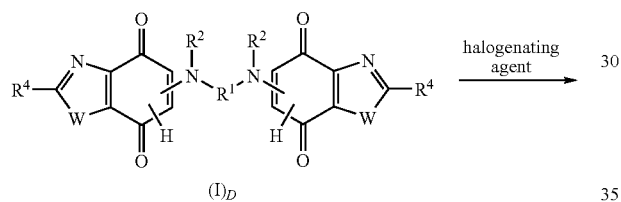

$(I)_D$

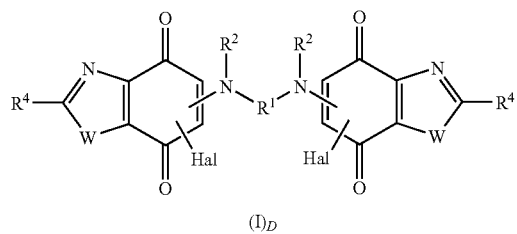

$(I)_D$ iv) Compounds of General Formula $(I)_{DM}$ or Compounds of General Formula $(I)_D$ where R5 Represents an Arylalkyl Radical:

iv.a) Compounds of General Formula $(I)_{DM}$ where R1 does not Represent $-(CH_2)_s-CO-NR^8-(CH_2)_t-$ and if $R^1$ Represents $(CH_2)_m-X-(CH_2)_n-$, then m=n and $R^5$ Does not Represent an Arylalkyl Radical:

The compounds of general formula $(I)_{DM}$ in which $R^2$, $R^3$, $R^4$, $R'^4$, W and W' are as described above and $R^1$ is as defined above but does not represent $-(CH_2)_s-CO-NR^8-(CH_2)_t-$ and if R1 represents $-(CH_2)_m-X-(CH_2)_n-$, then m=n and $R^5$ does not represent an arylalkyl radical, can be obtained according to the procedure summarized in Diagram 1c hereafter.

Diagram 1c

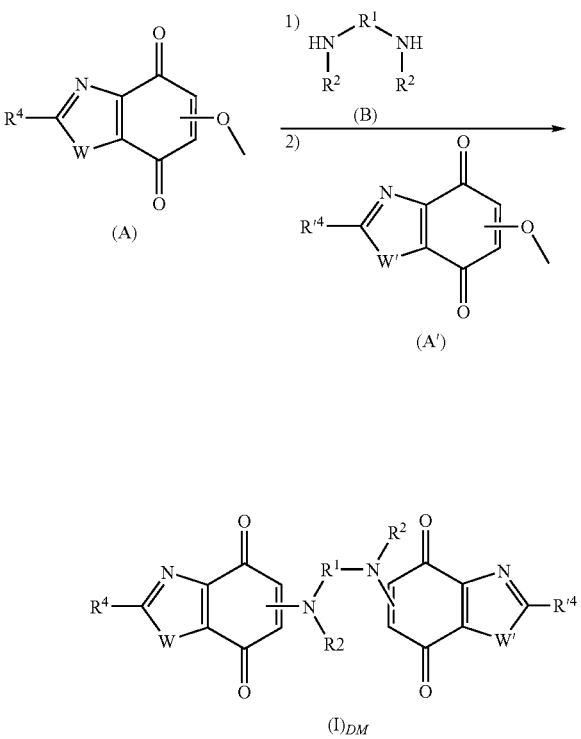

$(I)_{DM}$

According to this procedure, the compounds of general formula $(I)_{DM}$ are obtained by treatment of the intermediates of general formula (A) with a stoichiometric quantity or with a large excess of diamine of general formula (B) in a protic solvent such as methanol or ethanol, at a temperature preferably comprised between 20° C. and 80° C., followed by treatment with a stoichiometric quantity of the intermediates of general formula (A') such that $R'^4$ is different from $R^4$ and/or W' is different from W under the same conditions.

iv.b) Compounds of General Formula $(I)_{DM}$ where if $R^1$ Represents $-(CH_2)_m-X-(CH_2)_n-$, then m≠n or $R^5$ Represents an Arylalkyl Radical, and Compounds of General Formula $(I)_D$ Where if $R^1$ Represents $-(CH_2)_m-X-(CH_2)_n-$, then $R^5$ Represents Arylalkyl:

The compounds of general formula $(I)_{DM}$ in which $R^2$, $R^3$, $R^4$, $R'^4$, W and W' are as described above and in which, if $R^1$ represents $-(CH_2)_m-X-(CH_2)_n-$, then m≠n or $R^5$ represents arylalkyl, can be obtained according to the procedure summarized in Diagram 1d hereafter. The compounds of general formula $(I)_D$ in which W, $R^2$ and $R^4$ are as defined previously and such that if $R^1$ represents the $-(CH_2)_m-X-(CH_2)_n-$ radical and X represents $-NR^5-$ then $R^5$ represents an optionally substituted arylalkyl radical, can be obtained according to the procedure summarized in Diagram 1d hereafter (it being understood that in this case, W=W' and $R^4=R^{4'}$).

Diagram 1d

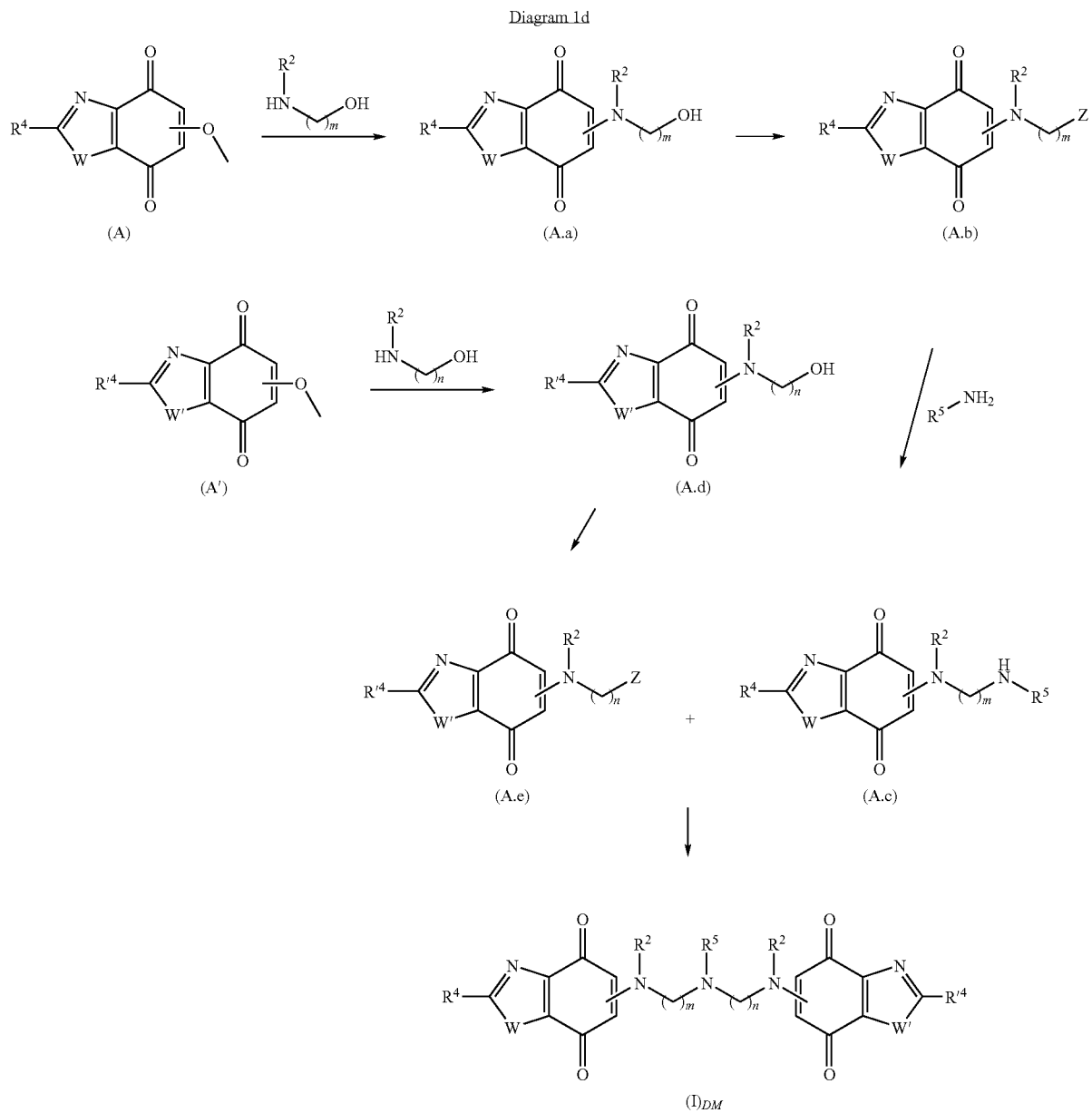

According to this method, the compounds of general formula (I)$_{DM}$ or (I)$_D$ are obtained by nucleophilic substitution of an intermediate of general formula (A.e) which carries a leaving group Z such as, for example, a methanesulphonate or toluenesulphonate group, or a halogen atom such as a bromine atom on a intermediate of general formula (A.c) in the presence of a base such as, for example diisopropylethylamine in a polar solvent such as, for example dimethylformamide. The intermediates of general formula (A.c) are obtained under the same conditions by nucleophilic substitution of the intermediates of general formula (A.b) by primary amines of general formula $R^5NH_2$. The intermediates of general formula (A.b) and (A.e) are obtained from the intermediates of general formula (A) and (A') respectively by reaction with amines of general formula $NHR^2$—$(CH_2)_m$—Br and $NHR^2$—$(CH_2)_n$—Br respectively, in a protic polar solvent such as methanol in the presence of a base such as triethylamine at a temperature preferably comprised between 20° C. and 80° C. The intermediates of general formula (A.b) and (A.e) can also be obtained from the intermediates of general formula (A.a) and (A.d) respectively by reaction with para-toluenesulphonyl chloride, for example in pyridine or in dichloromethane in the presence of triethylamine. The intermediates of general formula (A.a) and (A.d) are obtained by treatment of the intermediates of general formula (A) and (A') respectively, by the amines of general formula $NHR^2$—$(CH_2)_m$—OH and $NHR^2$—$(CH_2)_n$—OH respectively, in a protic solvent such as methanol or ethanol, at a temperature preferably comprised between 20° C. and 80° C.

iv.c) Compounds of General Formula (I)$_{DM}$ where $R^1$ Represents —$(CH_2)_s$—CO—$NR^8$—$(CH_2)_t$—:

The compounds of general formula (I)$_{DM}$ in which $R^2$, $R^3$, $R^4$, $R'^4$, W and W' are as described above and $R^1$ represents —$(CH_2)_s$—CO—$NR^8$—$CH_2N$—, can be obtained according to the procedure summarized in Diagram 1e hereafter.

Diagram 1e

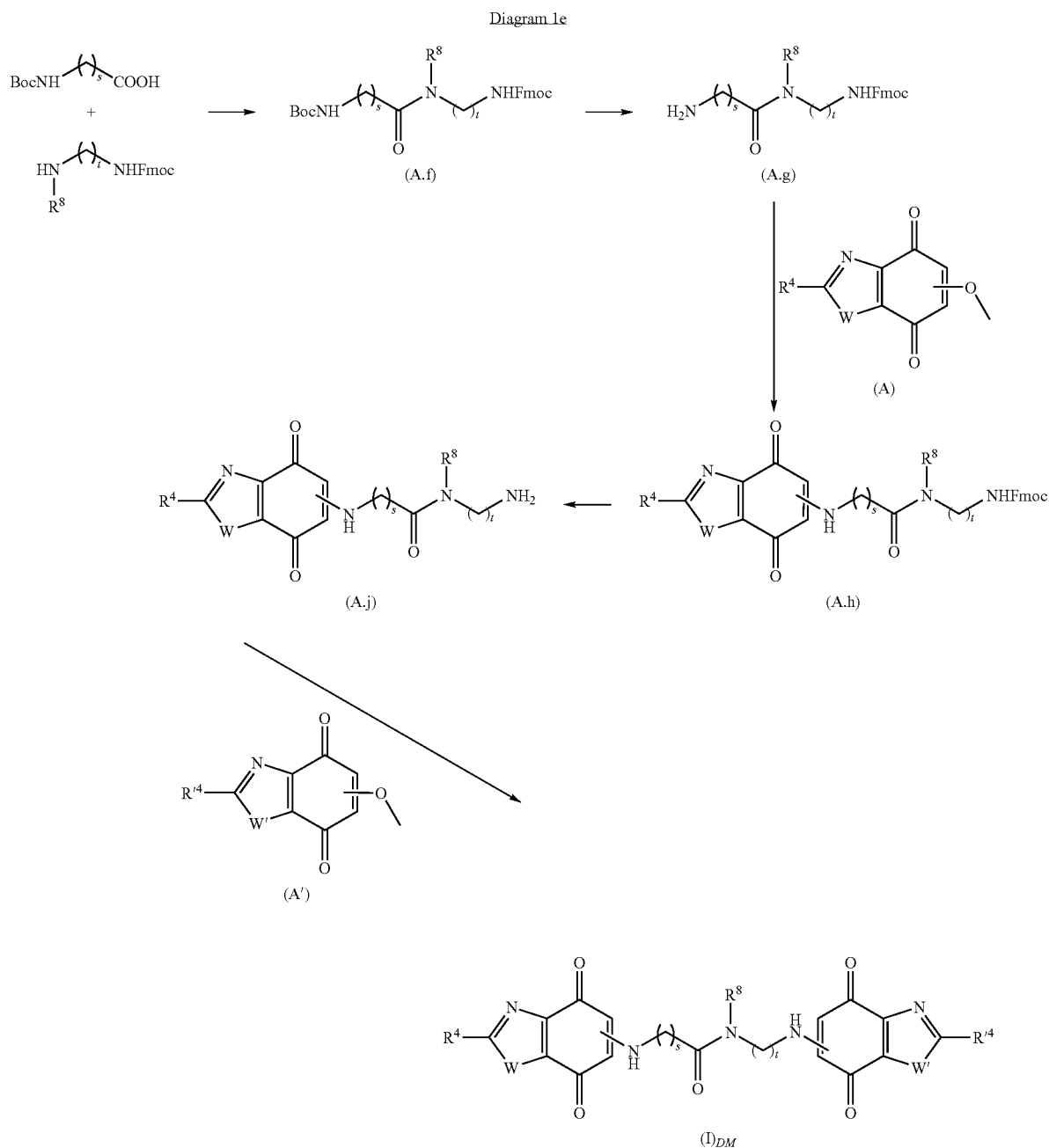

According to this procedure, the compounds of general formula (I)$_{DM}$ are obtained by treatment of the compounds of general formula (A') with amines of general formula (A.j) in a protic solvent such as methanol or ethanol at a temperature preferably comprised between 20° C. and 80° C. The intermediates of general formula (A.j) are themselves obtained, after deprotection of the terminal amine group according to methods known to a person skilled in the art, from the intermediates of general formula (A) on which the amines of general formula (A.g) are reacted under the conditions described above. The intermediates of general formula (A.g) are obtained by standard methods of peptide coupling followed by selective deprotection of the carbamate group which is also standard for a person skilled in the art.

Preparation of the Intermediates of General Formula (A) and (A'):

Given that the compounds of general formula (A') are the same as those of general formula (A), only the preparation of the compounds of general formula (A) is mentioned hereafter.

i) W Represents a Sulphur Atom:

When W represents a sulphur atom, the compounds of general formula (A), in which $R^4$ has the same meaning as in the general formula (I), can be obtained, Diagram 2, by oxidation of the compounds of general formula (A.ii) in which one of Q and Q' represents an amino radical and the other represents a hydrogen atom. The compounds to of general formula (A.ii) are obtained from the compounds of general formula (A.i), in which one of V and V' represents a nitro radical and the other represents a hydrogen atom, after reduction of the nitro group by the action of hydrogen in the presence of palladium on carbon or by the action of tin chloride.

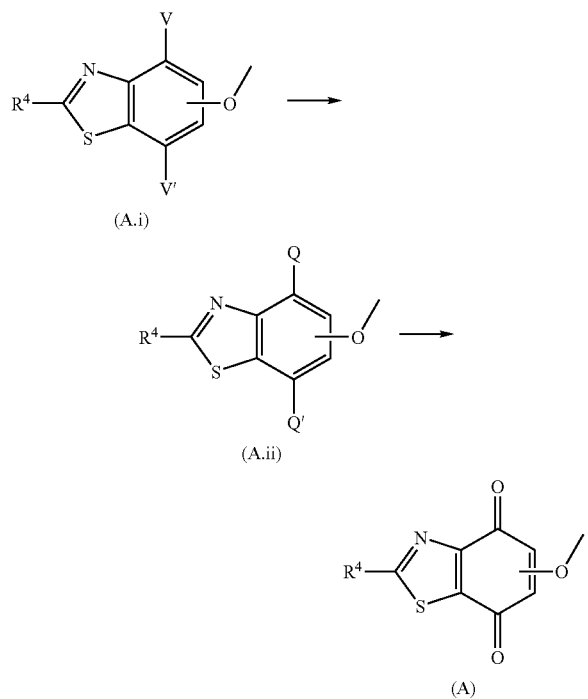

The compounds of general formula (A.i) can be synthesized according to methods already known to a person skilled in the art (see for example the Patent Application PCT WO 03/055868) or can be prepared according to the methods summarized in the Diagram s hereafter.

When the compounds of general formula (A.i) are such that their methoxy group is in position 5 of the benzothiazole ring, their preparation can be carried out according to the method summarized in Diagram 3 hereafter. According to said method, 5-methoxy-1,3-benzothiazol-2-amine (commercial) is converted, according to Sandmeyer's method, which is known to a person skilled in the art, to 2-bromo-5-methoxy-1,3-benzothiazole, itself nitrated according to methods known to a person skilled in the art in order to obtain 2-bromo-5-methoxy-4-nitro-1,3-benzothiazole. The intermediate of general formula (A.i) is then obtained by condensation with boronic acids, according to Suzuki's method, which is known to a person skilled in the art.

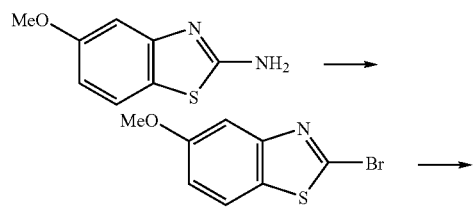

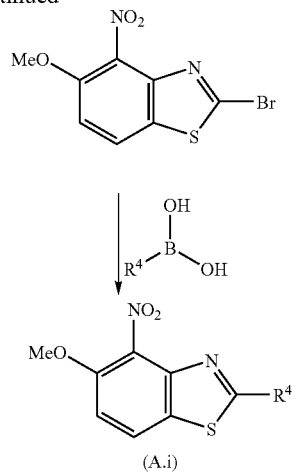

When the compounds of general formula (A.i) are such that their methoxy group is in position 6 of the benzothiazole ring, their preparation can be carried out according to the method summarized in Diagram 3a hereafter. According to said method, 6-methoxy-1,3-benzothiazol-2-amine (commercial) is converted, according to Sandmeyer's method, which is known to a person skilled in the art, to 2-bromo-6-methoxy-1,3-benzothiazole, itself nitrated according to methods known to a person skilled in the art in order to obtain 2-bromo-6-methoxy-7-nitro-1,3-benzothiazole. The intermediate of general formula (A.i) is then obtained by condensation with boronic acids, according to Suzuki's method, which is known to a person skilled in the art.

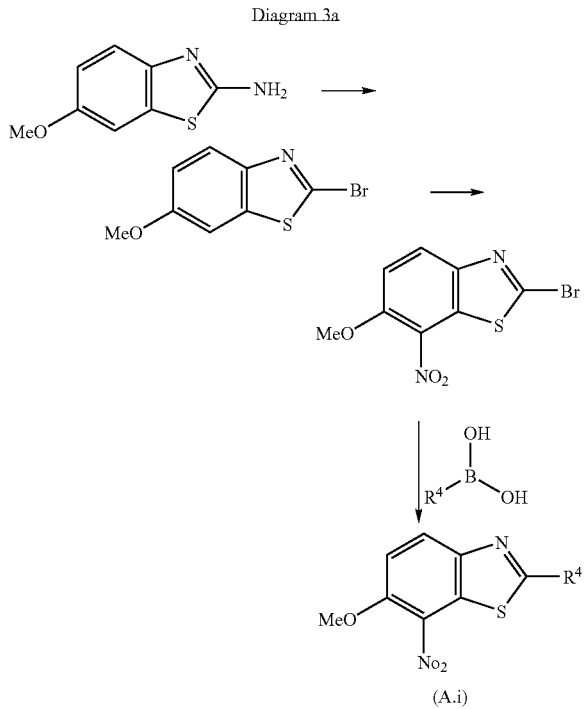

In the particular case where $R^4$ represents a —CO—NR$^{14}$R$^{15}$ radical, the intermediates of general formula (A.i) can be obtained, Diagram 4, from the compounds of general formula (A.iii), in which V and V' are as defined above, and the amines of general formula $R^{14}R^{15}NH$, by using the standard conditions for peptide synthesis (M. Bodansky, *The Practice of Peptide Synthesis*, 145 (Springer-Verlag, 1984)), for example in dichloromethane in the presence of a coupling reagent such as bromo-tris-pyrrolidino-phosphonium hexafluorophosphate (PyBroP) in the presence of dimethylaminopyridine (DMAP) (Coste et al., *Tetrahedron Lett.* (1990), 31, 669), or in a mixture (dimethylformamide/dichloromethane/dioxan: 1/1/1) in the presence of 1-(3-dimethylaminopropyl)-3-ethylcarbodiimide hydrochloride, diisopropylethylamine and a catalytic quantity of dimethylaminopyridine, or also by the formation of an intermediate acid chloride obtained by the addition of oxalyl chloride in solution to dichloromethane. As regards the compounds of general formula (A.iii) they can be obtained by oxidation of the carboxaldehydes of general formula (A.iv) by the action of a oxidizing agent such as, for example sodium chlorite in a buffered solution of sodium hydrogen phosphate (pH 3.5) and in an aqueous solution of tert-butanol in the presence of 2-methyl-2-butene; these aldehydes of general formula (A.iv) being themselves obtained by oxidation of the compounds of general formula (A.v) by the action, for example, of selenium oxide in 1,4-dioxan at 80° C. (Bu et al., *J. Med. Chem.* (2001), 44, 2004-2014). Finally, the compounds of general formula (A.v) in which V and V' are as defined above, can be obtained according to methods already known to a person skilled in the art (see for example the Patent Application PCT WO 03/055868).

Diagram 4

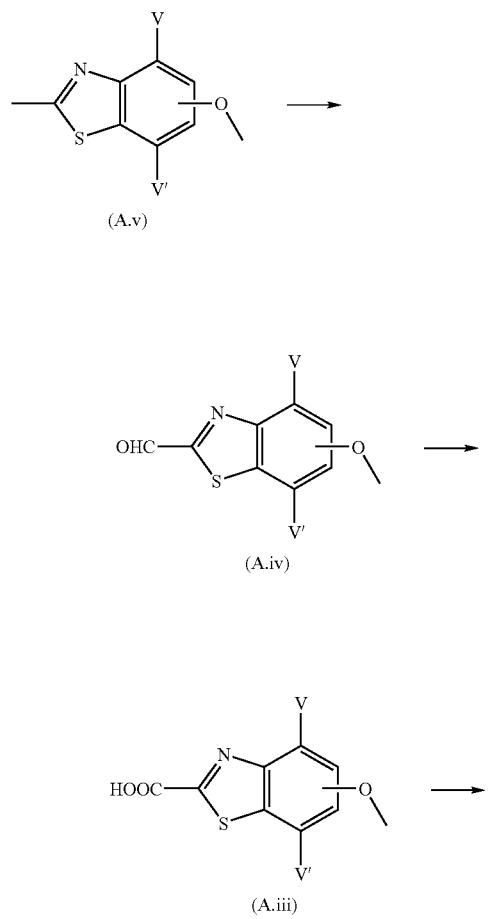

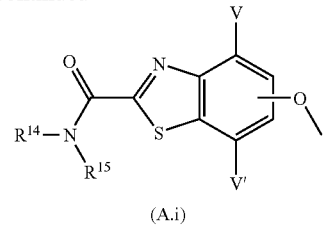

In the particular case where $R^4$ represents H, the intermediates of general formula (A) can be obtained by decarboxylation of the intermediates of general formula (A.iii), after heating of the latter for 2 hours at a temperature comprised between 40° C. and 80° C. in an organic solvent such as dichloromethane or acetonitrile.

In the particular case where $R^4$ represents a-$CH_2$—$NR^9R^{10}$ radical, the intermediates of general formula (A.i) can be obtained, Diagram 5, from the compounds of general formula (A.vi), in which V and V' are as defined above, and the amines of general formula $R^9R^{10}NH$, in a polar solvent in the presence of a base such as diisopropylethylamine and a catalytic quantity of sodium iodide. The compounds of general formula (A.vi) are obtained by nitration, according to standard methods known to a person skilled in the art, the intermediates of general formula (A.vii), themselves are obtained from the compounds of general formula (A.viii) which are subjected to a radicular bromination reaction using N-bromosuccinimide in the presence of an initiator such as 2.2'-azobis(2-methylpropionitrile) or dibenzoylperoxide in an aprotic solvent such as carbon tetrachloride ($CCl_4$) at a temperature preferably comprised between ambient temperature (i.e. approximately 25° C.) and 80° C. and under irradiation by a UV lamp (Mylari et al., *J. Med. Chem.* (1991), 34, 108-122).

Diagram 5

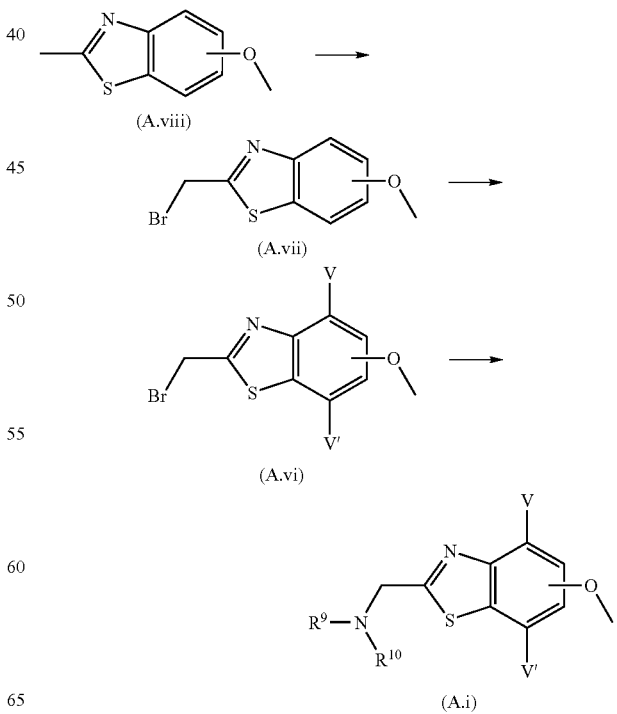

ii) W Represents an Oxygen Atom

When W represents an oxygen atom, the compounds of general formula (A), in which $R^4$ has the same meaning as in the general formula (I), can be obtained, Diagram 6, by oxidation of the compounds of general formula (A.ix) in which one of Q and Q' represents an amino radical and the other represents a hydrogen atom, or one of Q and Q' represents an hydroxyl radical and the other a hydrogen atom, according to methods known to a person skilled in the art (see for example the Patent Application PCT WO 03/055868). The compounds of general formula (A.ix) are themselves obtained by condensation of the compounds of general formula (A.x) in which Q and Q' have the same meaning as above with, for example, thioimidates of general formula (C) in a protic solvent such as ethanol at a temperature comprised between 25° C. and the boiling temperature of the solvent (according to the method described in particular by S. Rostamizadeh et al. *J. Chem Res, Synop,* 6, (2001), 227-228).

Diagram 6

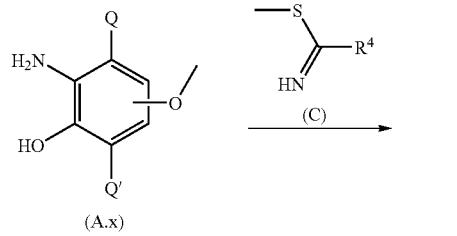

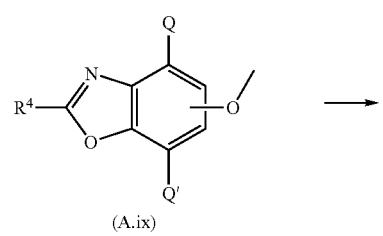

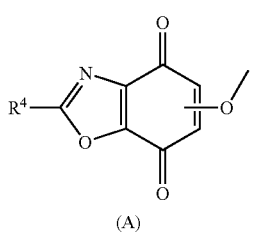

The compounds of general formula (A.x) can be obtained according to methods known to a person skilled in the art summarized in Diagram s 6a and 6b hereafter When the compounds of general formula (A.ix) are such that their methoxy group is in position 5 of the benzoxazole ring, the preparation of the compounds of general formula (A.x) can be carried out according to the method summarized in Diagram 6a hereafter. According to said method, 4-methoxy-2,6-dinitrophenol (described in particular by P. Cotelle and J.-P. Catteau, *Synth. Commun.,* 26, (1996), 4105-4112) is reduced, for example by the action of hydrogen in the presence of palladium on carbon, in order to produce the corresponding compound of general formula (A.x).

Diagram 6a

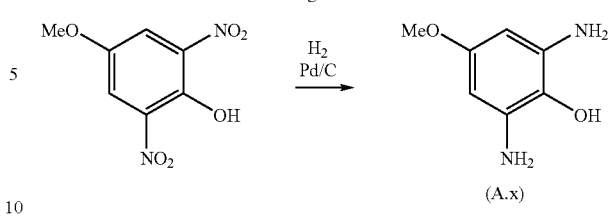

When the compounds of general formula (A.ix) are such that their methoxy group is in position 6 of the benzoxazole ring, the preparation of the compounds of general formula to (A.x) can be carried out according to the method summarized in Diagram 6b hereafter. According to said method, 5-methoxy-2-nitro-resorcinol (described in particular by J. F. Grove et al. *J. Chem. Soc.* (1956), 1956-1963) is reduced, for example by the action of hydrogen in the presence of palladium on carbon, in order to produce the corresponding compound of general formula (A.x).

Diagram 6b

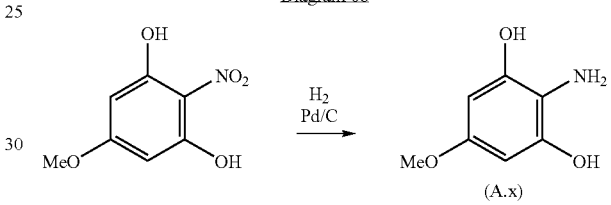

Preparation of the Amines of General Formula (B):

The amines of general formula (B) are commercially available or can be easily prepared according to current methods know to a person skilled in the art

EXAMPLES

As regards the temperatures to which reference is made in the present text, the term "approximately XX° C." indicates that the temperature in question corresponds to an interval within 10° C. above or below the temperature of XX° C., and preferably to an interval within 5° C. above or below the temperature of XX° C.

Unless otherwise defined, all the technical and scientific terms used here have the same meaning as that usually understood by an ordinary specialist in the field to which this invention belongs.

The following examples are presented in order to illustrate the above procedures and should in no event be considered as limiting the scope of the invention.

The melting points were measured using a Büchi 535 capillary apparatus.

The NMR spectra were recorded using a Brücker ARX 400 spectrometer. The chemical shifts are expressed in parts per million (ppm) with respect to tetramethylsilane (TMS) and the multiplicity of the signals is given in the form of a (singlet), d (doublet), t (triplet), m (multiplet).

Method Used for Measuring the Retention Time (R.T.) and the Molecular Peak (MH+)

The compounds are characterized by their retention time (r.t.), expressed in minutes, determined by liquid chromatography (LC), and their molecular peak (MH+) determined by mass spectrometry (MS), a single quadrupole mass spectrometer (Micromass, Platform model) equipped with an electrospray source is used with a resolution of 0.8 Da at 50% valley.

For Examples 1 to 56 hereafter, the elution conditions corresponding to the results indicated are the following: elution with the acetonitrile-water-trifluoroacetic acid mixture 50-950-0.2 (A) for 1 minute then passing from mixture (A) to an acetonitrile-water mixture 950-50 (B) by a linear gradient over a period of 7.5 minutes before elution with pure mixture B for 2 minutes.

Example 1

5.5'-[(methylimino)bis(propane-3,1-diylimino)]bis(2-methyl-1,3-benzothiazole-4,7-dione)

83.4 mg (0.57 mmol; 0.6 equivalents) of N-(3-aminopropyl)-N-methylpropane-1,3-diamine are added to 200 mg (0.95 mmol) of 5-methoxy-2-methyl-4,7-dioxobenzothiazole in solution in 15 ml of anhydrous ethanol. The reaction mixture is stirred at 60° C. for 2 hours, then the solvent is evaporated off under reduced pressure. The residue is purified on a silica column (eluent: methanol at 3% in dichloromethane) and 30 mg (yield=36%) of expected product is obtained in the form of a red powder. Melting point: 94-96° C.
NMR $^1$H (DMSO d6, 400 MHz, δ): 7.93 (t, 2H, 2NH); 5.40 (s, 2H, 2CH); 3.20-3.15 (m, 4H); 2.72 (s, 6H, 2CH$_3$); 2.40-2.37 (m, 4H); 2.17 (s, 3H, CH$_3$); 1.76-1.73 (m, 4H).
MS-LC: MH+=500.15; r.t.=7.49 min.

The compounds of Examples 2 to 4 is obtained in a similar way to that used for Example 1, with the suitable amine replacing N-(3-aminopropyl)-N-methylpropane-1,3-diamine.

Example 2

5.5'-[(methylimino)bis(ethane-2,1-diylimino)]bis(2-methyl-1,3-benzothiazole-4,7-dione)

Red powder. Melting point: 188-190=C.
NMR $^1$H (DMSO d6, 400 MHz, δ): 7.32 (t, 2H, 2NH); 5.43 (s, 2H, 2CH); 3.23-3.19 (m, 4H); 2.72 (s, 6H, 2CH$_3$); 2.66-2.62 (m, 4H); 2.31 (s, 3H, CH$_3$).
MS-LC: MH+=472.18; r.t.=7.31 min.

Example 3

5.5'-[oxybis(ethane-2,1-diylimino)]bis(2-methyl-1,3-benzothiazole-4,7-dione)

Red powder.
NMR $^1$H (DMSO d6, 400 MHz, δ): 7.53 (t, 2H, 2NH); 5.50 (s, 2H, 2CH); 3.66-3.64 (m, 4H, 2CH$_2$); 3.30-3.29 (m, 4H, 2CH$_2$); 2.74 (s, 6H, 2CH$_3$).
MS-LC: MH+=459.06; r.t.=8.20 min.

Example 4

5.5'-pentane-1,5-diyldiimino)bis(2-methyl-1,3-benzothiazole-4,7-dione)

Red powder.
NMR $^1$H (DMSO d6, 400 MHz, δ): 7.74 (t, 2H, 2NH); 5.45 (s, 2H, 2CH); 3.17-3.12 (m, 4H, 2CH$_2$); 2.74 (s, 6H, 2CH$_3$); 1.61-1.56 (m, 4H, 2CH$_2$); 1.36-1.33 (m, 2H, CH$_2$).
MS-LC: MH+=457.11; r.t.=8.97 min.

The compounds of Examples 5 and 6 are obtained in a similar way to that used for Example 1, with 6-methoxy-2-methyl-4,7-dioxobenzothiazole replacing 5-methoxy-2-methyl-4,7-dioxobenzothiazole and the suitable amine replacing N-(3-aminopropyl)-N-methylpropane-1,3-diamine in the case of Example 6.

Example 5

6.6'-[(methylimino)bis(propane-3,1-diylimino)]bis(2-methyl-1,3-benzothiazole-4,7-dione)

Red powder. Melting point: 91-93° C.
NMR $^1$H (DMSO d6, 400 MHz, δ): 7.80 (t, 2H, 2NH); 5.34 (s, 2H, 2CH); 3.20-3.15 (m, 4H); 2.76 (s, 6H, 2CH$_3$); 2.39-2.37 (m, 4H); 2.17 (s, 3H, CH$_3$); 1.76-1.73 (m, 4H).
MS-LC: MH+=500.35; r.t.=7.43 min.

Example 6

6.6'-[(methylimino)bis(ethane-2,1-diylimino)]bis(2-methyl-1,3-benzothiazole-4,7-dione)

Red powder.
NMR $^1$H (DMSO d6, 400 MHz, δ): 7.13 (t, 2H, 2NH); 5.37 (s, 2H, 2CH); 3.23-3.19 (m, 4H); 2.77 (s, 6H, 2CH$_3$); 2.66-2.61 (m, 4H); 2.32 (s, 3H, CH$_3$).
MS-LC: MH+=472.30; r.t.=7.17 min.

The compounds of Examples 7 to 16 are obtained in a similar way to that used for Example 1, with the suitable quinone replacing 5-methoxy-2-methyl-4,7-dioxobenzothiazole.

Example 7

5.5'-[(methylimino)bis(propane-3,1-diylimino)]bis{4,7-dioxo-N-[3-(2-oxopyrrolidin-1-yl)propyl]-4,7-dihydro-1,3-benzothiazole-2-carboxamide}

Red powder. Melting point: 185-186° C.
NMR $^1$H (DMSO d6, 400 MHz, δ): 9.11 (t, 2H, 2NH); 8.18 (t, 2H, 2NH); 5.54 (s, 2H, 2CH); 3.37-3.18 (m, 16H); 2.40 (m, 4H); 2.22 (m, 4H); 2.18 (s, 3H, CH$_3$); 1.92 (m, 4H); 1.74 (m, 8H).
MS-LC: MH+=808.51; r.t.=7.61 min.

Example 8

6.6'-[(methylimino)bis(propane-3,1-diylimino)]-bis[2-(2,5-difluorophenyl)-1,3-benzoxazole-4,7-dione]

Red powder. Melting point: 209-210° C.
NMR $^1$H (DMSO d6, 400 MHz, δ): 8.00 (m, 2H, arom H.); 7.82 (m, 2H, 2NH); 7.55-7.50 (4H, arom H.); 5.31 (s, 2H, 2CH); 3.22-3.19 (m, 4H); 2.48-2.44 (m, 4H); 2.22 (s, 3H, CH$_3$); 1.80-1.77 (m, 4H).
MS-LC: MH+=664.40; r.t.=8.81 min.

Example 9

6.6'-[(methylimino)bis(propane-3,1-diylimino)]-bis[2-(3,5-dibromophenyl)-1,3-benzoxazole-4,7-dione]

Red powder. Melting point: 227-228° C.
NMR $^1$H (CF$_3$COOD, 400 MHz, δ): 7.94 (m, 4H, arom H.); 7.69 (m, 2H, arom H.); 4.94 (s, 2H, 2CH); 3.34-3.27 (m, 6H); 3.20-3.13 (m, 2H); 2.84 (s, 3H, CH$_3$); 2.17-2.06 (m, 4H).
MS-LC: MH+=903.90; r.t.=10.11 min.

Example 10

6.6'-[(methylimino)bis(propane-3,1-diylimino)]bis[2-(2-chloro-6-fluorobenzyl)-1,3-benzoxazole-4,7-dione]

Red powder. Melting point: 165-167° C.
NMR $^1$H (DMSO d6, 400 MHz, δ): 7.87 (t, 2H, 2NH); 7.48-7.39 (m, 4H, arom H.); 7.34-7.29 (m, 2H, arom H.); 5.25 (s, 2H, 2CH); 4.46 (s, 4H, 2CH$_2$); 3.18-3.13 (m, 4H); 2.38-2.36 (m, 4H); 2.15 (s, 3H, CH$_3$); 1.73-1.70 (m, 4H).
MS-LC: MH+=724.44; r.t.=9.13 min.

Example 11

6.6'-[(methylimino)bis(propane-3,1-diylimino)]-bis[2-(3-bromophenyl)-1,3-benzoxazole-4,7-dione]

Red powder. Melting point: 199-200° C.
NMR $^1$H (DMSO d6, 400 MHz, δ): 8.08-8.00 (m, 6H, arom H.); 7.81-7.79 (m, 2H, arom H.); 7.54-7.50 (m, 2H, 2NH); 5.29 (s, 2H, 2CH); 3.21-3.16 (m, 4H); 2.42 (m, 4H); 2.20 (s, 3H, CH$_3$); 1.80-1.77 (m, 4H).
MS-LC: MH+=748.21; r.t.=9.37 min.

Example 12

6.6'-[(methylimino)bis(propane-3,1-diylimino)]-bis[2-(4-bromophenyl)-1,3-benzoxazole-4,7-dione]

Red powder. Melting point: 233-234° C.
NMR $^1$H (CF$_3$COOD, 400 MHz, δ): 7.76-7.74 (m, 4H, arom H.); 7.49-7.47 (m, 4H, arom H.); 3.34-3.26 (m, 6H); 3.20-3.12 (m, 2H); 2.83 (s, 3H, CH$_3$); 2.13-2.06 (m, 4H).
MS-LC: MH+=748.22; r.t.=9.20 min.

Example 13

6.6'-[(methylimino)bis(propane-3,1-diylimino)]-bis[2-(3,5-difluorophenyl)-1,3-benzoxazole-4,7-dione]

Red powder.
NMR $^1$H (DMSO d6, 400 MHz, δ): 8.20-8.17 (m, 2H); 7.61-7.58 (m, 4H); 7.52-7.47 (m, 2H); 5.31 (s, 2H, 2CH); 3.21-3.17 (m, 4H); 2.44-2.41 (m, 4H); 2.20 (s, 3H, CH$_3$); 1.82-1.76 (m, 4H).
MS-LC: MH+=664.30; r.t.=9.06 min.

Example 14

6.6'-[(methylimino)bis(propane-3,1-diylimino)]-bis[2-(3-chlorophenyl)-1,3-benzoxazole-4,7-dione]

Red powder. Melting point: 196-197° C.
NMR $^1$H (DMSO d6, 400 MHz, δ): 8.00-7.95 (m, 6H, 6 arom.); 7.68-7.66 (m, 2H, arom to H.); 7.58 (t, 2H, 2NH); 5.29 (s, 2H, 2CH); 3.21-3.16 (m, 4H); 2.43 (m, 4H); 2.21 (m, 3H, CH$_3$); 1.80-1.77 (m, 4H).
MS-LC: MH+=660.26; r.t.=9.11 min.

Example 15

6.6'-[(methylimino)bis(propane-3,1-diylimino)]-bis[2-(4-fluorophenyl)-1,3-benzoxazole-4,7-dione]

Red powder. Melting point: 204-205° C.
NMR $^1$H (DMSO d6, 400 MHz, δ): 8.10-8.06 (m, 4H, arom H.); 7.96 (t, 2H, 2NH); 7.41-7.37 (m, 4H, arom H.); 5.28 (s, 2H, 2CH); 3.21-3.16 (m, 4H); 2.44 (m, 4H); 2.21 (m, 3H, CH$_3$); 1.80-1.77 (m, 4H).
MS-LC: MH+=628.32; r.t.=8.70 min.

Example 16

6.6'-[(methylimino)bis(propane-3,1-diylimino)]bis[2-(4-bromo-3-methylphenyl)-1,3-benzoxazole-4,7-dione]

Red powder.
MS-LC: MH+=776.17; r.t.=9.76 min.

Example 17

5.5'-[(methylimino)bis(propane-3,1-diylimino)]bis(6-bromo-2-methyl-1,3-benzothiazole-4,7-dione)

70 mg (0.2 mmol) of the compound of Example 1 are solubilized in 10 ml of acetic acid. 55 mg (4.4 mmol; 2.2 eq.) of N-bromosuccinimide is added and the reaction mixture is stirred for 1 hour at ambient temperature. After concentration under reduced pressure, the residue is purified by chromatography on a silica column (eluent: dichloromethane/methanol 95/5) and the expected product is obtained, after taking up in ethyl ether and filtration, in the form of a violet powder.
NMR $^1$H (DMSO d6, 400 MHz, δ): 7.99 (s, 2H, 2NH); 3.83-3.79 (m, 4H); 2.72 (s, 6H, 2CH$_3$); 2.47-2.44 (m, 4H); 2.19 (s, 3H, CH$_3$); 1.78 (m, 4H).
SM-LC: MH+=655.96; r.t.=7.83 min.

The compound of Example 18 is obtained in a similar way to that used for Example 1, with the suitable triamine replacing N-(3-aminopropyl)-N-methylpropane-1,3-diamine.

Example 18

5.5',5''-[nitrilotripropan-3,1-diylimino)]tris(2-methyl-1,3-benzothiazole-4,7-dione)

Red powder. Melting point=131-132° C.
NMR 1H (DMSO d6, 400 MHz, δ): 784-7.81 (m, 3H); 5.38 (s, 3H); 318-3.13 (m, 6H); 2.71 (s, 9H, 3CH$_3$); 249-2.45 (m, 6H); 179-1.74 (m, 6H).
MS-LC: MH+=720.24; r.t.=7.70 min.

The compounds of Examples 19 to 22 are obtained in a similar way to that used for Example 1, with the suitable diamine replacing N-(3-aminopropyl)-N-methylpropane-1,3-diamine.

Example 19

5.5'-(2,2-dimethylpropane-1,3-diyldiimino)bis(2-methyl-1,3-benzothiazole-4,7-dione)

Red powder.
MS-LC: MH+=457.17; r.t.=8.88 min.

Example 20

5.5'-[cyclohexane-1,4-diylbis(methyleneimino)]bis(2-methyl-1,3-benzothiazole-4,7-dione)

Red powder. Melting point>240° C.
The compounds of Examples 23 and 24 are obtained in a similar way to that used for Example 1, with the suitable diamine replacing N-(3-aminopropyl)-N-methylpropane-1, 3-diamine and 2-(2,5-difluorophenyl)-6-methoxy-1,3-benzoxazole-4,7-dione replacing 5-methoxy-2-methyl-4,7-dioxobenzothiazole.

Example 23

6.6'-{(methylimino)bis[propane-3,1-diyl(methylimino)]}bis[2-(2,5-difluorophenyl)-1,3-benzoxazole-4,7-dione]

Powder violet foncé.
NMR $^1$H (DMSO d6, 400 MHz, δ): 7.85-7.81 (m, 2H); 7.57-7.48 (m, 4H); 5.49 (s, 2H); 3.66-3.63 (m, 4H); 3.06 (s, 6H, 2CH$_3$); 2.33-2.29 (m, 4H); 2.09 (s, 3H, CH$_3$); 1.78-1.74 (m, 4H).
MS-LC: MH+=692.34; r.t.=8.76 min.

Example 24

N$^3$-[2-(2,5-difluorophenyl)-4,7-dioxo-4,7-dihydro-1,3-benzoxazol-6-yl]-N$^1$-(3-{[2-(2,5-difluorophenyl)-4,7-dioxo-4,7-dihydro-1,3-benzoxazol-6-yl]amino}propyl)-β-alaninamide Red powder.
MS-LC: MH+=664.29; r.t.=9.90 min.

Example 25

5.5'-[(methylimino)bis(propane-3,1-diylimino)]bis(1,3-benzothiazole-4,7-dione)

25.1) 5-methoxy-4-nitro-1,3-benzothiazole 25.1.1) 5-methoxy-4-nitro-1,3-benzothiazole-2-carbaldehyde:

12.8 g (0.115 mol; 6 equivalents) of selenium dioxide is added to 4.34 g (19.3 mmol) of 5-methoxy-2-methyl-4-nitro-1,3-benzothiazole in solution in 180 ml of anhydrous dioxan. The reaction mixture is stirred at 80° C. for 18 hours then the insoluble part is filtered and the solvent is evaporated off under reduced pressure. The expected aldehyde is obtained in the form of a yellow oil and purified on a silica column (eluent: ethyl acetate/heptane: gradient of 30% to 70%). Melting point: 154-155° C.
NMR $^1$H (DMSO d6, 400 MHz, δ): 10.06 (s, 1H, CHO); 8.52-8.49 (d, 1H, arom H); 7.80-7.78 (d, 2H, arom H); 4.04 (s, 3H, OCH$_3$).

25.1.2) Acid 5-methoxy-4-nitro-1,3-benzothiazole-2-carboxylic

A solution of 18 g of sodium chlorite and 18 g of sodium hydrogen phosphate in 180 ml of water is added dropwise to the carbaldehyde residue taken up in 420 ml of tert-butanol and 100 ml of 2-methyl-but-2-ene. The reaction mixture is maintained under stirring for 18 hours at ambient temperature, then the insoluble part is filtered, taken up in water and the aqueous solution obtained is acidified by a 1M solution of hydrochloric acid. The precipitate obtained is filtered and washed with water. The acid is obtained in the form of a beige powder. (m=3.12 g; yield=64%). Melting point: 140-142° C.
NMR $^1$H (DMSO d6, 400 MHz, δ): 8.45-8.43 (d, 1H, arom H); 7.74-7.71 (d, 1H, arom H); 3.99 (s, 3H, CH$_3$).
MS-LC: MH+=254.99; r.t.=8.20 min.

25.1.3) 5-methoxy-4-nitro-1,3-benzothiazole 3 g (11.8 mmol) of 5-methoxy-4-nitro-1,3-benzothiazole-2-carboxylic acid is suspended in 200 ml of dichloromethane and heated at 60° C. for 2 hours. The dichloromethane is evaporated off under reduced pressure. 5-methoxy-4-nitro-1,3-benzothiazole is obtained in the form of a beige powder. (m=2 g; yield=80%).
NMR $^1$H (DMSO d6, 400 MHz, δ): 9.53 (s, 1H); 8.35 (d, 1H); 7.60 (s, 1H).
MS-LC: MH+=211.01; r.t.=9.30 min.

25.2) 5-methoxy-1,3-benzothiazol-4-amine 730 mg (3.5 mmol) of 5-methoxy-4-nitro-1,3-benzothiazole is solubilized in 50 ml of methanol and 73 mg (10%) of palladium on carbon is added to the reaction mixture which is maintained under stirring under 2.5 bars of hydrogen for 18 hours. The catalyst is filtered out, then the solvent is evaporated off under reduced pressure. 248 mg (yield=40%) of 5-methoxy-1,3-benzothiazol-4-amine is obtained and used in the following stage without other purification.
MS-LC: MH+=181.08; r.t.=7.97 min.

25.3) 5-methoxy-1,3-benzothiazol-4,7-dione 1.34 g (2.5 mmol; 1.8 equivalent) of Fremy's salt (potassium nitrosodisulphonate, containing 25 to 50% of water and methanol) in solution in 40 ml of a 0.3 M solution of sodium hydrogen phosphate, is added to a solution of 248 mg (1.4 mmol) of 5-methoxy-1,3-benzothiazole-4-amine in 9 ml of acetone. The reaction mixture is maintained under stirring at ambient temperature for 3 hours, then concentrated under reduced pressure. The product formed is extracted with 3 times 50 ml of dichloromethane and the aqueous phase is washed with 50 ml of a solution of water saturated with sodium chloride. The organic phases are combined, dried over sodium sulphate and the solvent is evaporated off under reduced pressure. 248 mg (yield=91%) of 5-methoxy-1,3-benzothiazol-4,7-dione is obtained and used in the following stage without other purification.
MS-LC: MH+=196.05; r.t.=7.65 min.

25.4) 5.5'-[(methylimino)bis(propane-3,1-diylimino)]bis(1,3-benzothiazole-4,7-dione)

57 µl (0.37 mmol; 0.48 equivalent) of N-(3-aminopropyl)-N-methylpropane-1,3-diamine is added to 150 mg (0.77 mmol) of 5-methoxy-1,3-benzothiazol-4,7-dione in solution in 6 ml of ethanol. The reaction mixture is maintained under stirring at 85° C. for 90 minutes, then the solvent is evaporated off under reduced pressure and the expected product is purified by chromatography on a silica column (eluent: dichloromethane/methanol mixture 94/6) and 95 mg (yield=26%) of 5.5'-[(methylimino)bis(propane-3,1-diylimino)]bis(1,3-benzothiazole-4,7-dione) is obtained in the form of a red powder. Melting point: 223-224° C.
NMR $^1$H (DMSO d6, 400 MHz, δ): 9.28 (s, 2H); 8.02 (t, 2H, 2NH); 5.48 (s, 2H); 3.24-3.19 (m, 4H); 2.42-2.38 (m, 4H); 2.18 (s, 3H, CH$_3$); 1.78-1.74 (m, 4H).
MS-LC: MH+=472.19; r.t.=7.32 min.

Example 26

5,5'-[(methylimino)bis(propane-3,1-diylimino)]bis[2-(morpholin-4-ylcarbonyl)-1,3-benzothiazole-4,7-dione]

26.1) 5-methoxy-4-nitro-1,3-benzothiazole-2-carboxylic acid 26.1.1) 5-methoxy-4-nitro-1,3-benzothiazole-2-carbaldehyde:

The experimental protocol is described in Stage 25.1.1 of Example 25.

26.1.2) 5-methoxy-4-nitro-1,3-benzothiazole-2-carboxylic acid

The experimental protocol is described in Stage 25.1.2 of Example 25.

26.2) 5-methoxy-2-(morpholin-4-ylcarbonyl)-1,3-benzothiazole-4,7-dione 26.2.1) 5-methoxy-2-(morpholin-4-ylcarbonyl)-4-nitro-1,3-benzothiazole:

980 mg (2.1 mmol; 1.1 eq.) of bromo-tris-pyrrolidino-phosphonium hexafluorophosphate (PyBroP) is added to 500 mg (1.97 mmol) of 5-methoxy-4-nitro-1,3-benzothiazole-2-carboxylic acid and 344 µl (1.97 mmol; 1 eq.) of diisopropylethylamine in solution in 40 ml of dichloromethane. The reaction mixture is maintained for 15 minutes under stirring at ambient temperature, then 202 µl (2.3 mmol; 1.2 eq.) of morpholine and a spatula tip's worth of dimethylaminopyridine are added to the medium which is maintained under stirring for 18 hours at ambient temperature. An insoluble part is then filtered and the solvent evaporated off under reduced pressure. The residue is then purified on a silica column (eluent: ethyl acetate/heptane: gradient of 30 to 70% over 40 minutes then for 5 minutes at 70% of ethyl acetate in heptane) and 210 mg (yield=33%) of expected product is obtained in the form of beige powder.

MS-LC: MH+=324.01; r.t.=9.63 min.

26.2.2) 5-methoxy-2-(morpholin-4-ylcarbonyl)-1,3-benzothiazol-4-amine 20 mg of 10% palladium on activated carbon is added to 210 mg (0.65 mmol) of 5-methoxy-2-(morpholin-4-ylcarbonyl)-4-nitro-1,3-benzothiazole in solution in 10 ml of methanol. The reaction medium is then placed under stirring under a hydrogen atmosphere for 18 hours. The catalyst is then filtered out and the solvent evaporated off. 173 mg of the expected product (crude yield=91%) is obtained in the form of a yellow oil and is used in the following stage without other purification.

MS-LC: MH+=294.04; r.t.=9.09 min.

26.2.3) 5-methoxy-2-(morpholin-4-ylcarbonyl)-1,3-benzothiazole-4,7-dione

A solution of 570 mg (1.063 mmol; 1.8 eq.) of Fremy's salt (potassium nitrosodisulphonate, containing from 25 to 50% of water and methanol) in a 0.3M aqueous solution of sodium hydrogen phosphate (12 ml) is added dropwise to 173 mg (0.6 mmol) of 5-methoxy-2-(morpholin-4-ylcarbonyl)-1,3-benzothiazol-4-amine in solution in 5 ml of acetone. The reaction mixture is maintained under stirring at ambient temperature for 4 hours, then the acetone is evaporated off and the medium is taken up in 10 ml of dichloromethane and washed twice with 7 ml of a saturated aqueous solution of sodium chloride. The organic phases are combined, dried over magnesium sulphate and the solvent evaporated off under reduced pressure. 175 mg (yield brut=99%) of expected product is obtained in the form of a yellow powder and is used in the following stage without other purification.

MS-LC: MH+=308.99; r.t.=8.40 mm.

26.3) 5,5'-[(methylimino)bis(propane-3,1-diylimino)]bis[2-(morpholin-4-ylcarbonyl)-1,3-benzothiazole-4,7-dione]

51 µl (0.32 mmol; 0.5 equivalent) of N-(3-aminopropyl)-N-methylpropane-1,3-diamine is added to 200 mg (0.65 mmol) of 5-methoxy-2-(morpholin-4-ylcarbonyl)-1,3-benzothiazole-4,7-dione in solution in 15 ml of ethanol. The reaction mixture is maintained under stirring at 85° C. for 2 hours, then the solvent is evaporated off under reduced pressure and the expected product is purified by chromatography on a silica column (eluent: dichloromethane/methanol mixture 95/5) then recrystallized from a mixture of acetone and ethyl ether and 110 mg (yield=24%) of 5,5'-[(methylimino)bis(propane-3,1-diylimino)]bis[2-(morpholin-4-ylcarbonyl)-1,3-benzothiazole-4,7-dione] is obtained in the form of a red powder. Melting point=207-208° C.

NMR $^1$H (DMSO d6, 400 MHz, δ): 8.17 (m, 2H, 2NH); 5.52 (s, 2H, 2CH); 4.25 (m, 4H); 3.69 (m, 12H); 3.25-3.20 (m, 4H); 2.42 (m, 4H); 2.20 (s, 3H, CH$_3$); 1.79-1.76 (m, 4H).

MS-LC: MH+=698.30; r.t.=7.66 min.

The compounds of Examples 27 to 37 are obtained in a similar way to that used for Example 26, with the suitable amine replacing morpholine in the third stage and 6-methoxy-2-methyl-7-nitro-1,3-benzothiazole replacing 5-methoxy-2-methyl-4-nitro-1,3-benzothiazole in the first stage for Example 31.

Example 27

5,5'-[(methylimino)bis(propane-3,1-diylimino)]bis(2-{[4-(morpholin-4-ylcarbonyl)piperazin-1-yl]carbonyl}-1,3-benzothiazole-4,7-dione)

Red powder. Melting point=157-158° C.
NMR $^1$H (DMSO d6, 400 MHz, δ): 8.19 (t, 2H, 2NH); 5.52 (s, 2H, 2CH); 4.24 (m, 4H); 3.68 (m, 4H); 3.57 (m, 10H); 3.25-3.22 (m, 4H); 3.21-3.20 (m, 4H); 3.18-3.16 (m, 10H); 3.44-3.41 (m, 4H); 2.20 (s, 3H, CH$_3$); 1.79-1.76 (m, 4H).
MS-LC: MH+=922.43; r.t.=7.60 min.

Example 28

5,5'-[(methylimino)bis(propane-3,1-diylimino)]bis(2-{[4-(tetrahydrofuran-2-ylcarbonyl)piperazin-1-yl]carbonyl}-1,3-benzothiazole-4,7-dione)

Red powder. Melting point=152-153° C.
NMR $^1$H (DMSO d6, 400 MHz, δ): 8.20 (t, 2H, 2NH); 5.52 (s, 2H, 2CH); 4.70 (t, 2H); 4.40-4.10 (m, 4H); 3.80-3.50 (m, 16H); 3.28-3.22 (m, 4H); 2.43-2.40 (m, 4H); 2.20 (s, 3H, CH$_3$); 2.03-2.01 (m, 4H); 1.84-1.76 (m, 8H).
MS-LC: MH+=892.56; r.t.=7.58 min.

Example 29

5,5'-[(methylimino)bis(propane-3,1-diylimino)]bis
(2-{[4-(methylsulphonyl)piperazin-1-yl]carbonyl}-1,
3-benzothiazole-4,7-dione)

Red powder.
MS-LC: MH+=852.42; r.t.=7.89 min.

Example 30

5,5'-[(methylimino)bis(propane-3,1-diylimino)]bis
[N-(4-methoxyphenyl)-4,7-dioxo-4,7-dihydro-1,3-
benzothiazole-2-carboxamide]

Red powder.
MS-LC: MH+=770.38; r.t.=8.87 min.

Example 31

6,6'-[(methylimino)bis(propane-3,1-diylimino)]bis
[2-(pyrrolidin-1-ylcarbonyl)-1,3-benzothiazole-4,7-
dione]

Red powder. Melting point=237-238° C.
NMR $^1$H (DMSO d6, 400 MHz, δ): 7.91 (t, 2H, 2NH); 5.45 (s, 2H, 2CH); 3.98 (t, 4H); 3.54 (t, 4H); 3.20-3.18 (m, 4H); 2.40 (t, 4H); 2.18 (s, 3H, CH$_3$); 1.97-1.94 (m, 4H); 1.87-1.84 (m, 4H); 1.78-1.74 (m, 4H).
MS-LC: MH+=666.32; r.t.=7.91 min.

Example 32

5,5'-[(methylimino)bis(propane-3,1-diylimino)]bis
[N-(4-fluorophenyl)-4,7-dioxo-4,7-dihydro-1,3-ben-
zothiazole-2-carboxamide]

Red powder. Melting point=262-263° C.
NMR $^1$H (DMSO d6, 400 MHz, δ): 11.00 (s, 2H, 2NH); 8.26 (t, 2H, 2NH); 7.85-7.82 (m, 4H); 7.20-7.15 (m, 4H); 5.56 (s, 2H, 2CH); 3.25-3.23 (m, 4H); 2.44-2.41 (m, 4H); 2.20 (s, 3H, CH$_3$); 1.81-1.78 (m, 4H).
MS-LC: MH+=746.27; r.t.=9.15 min.

Example 33

5,5'-[(methylimino)bis(propane-3,1-diylimino)]bis
[N-(4-methoxybenzyl)-4,7-dioxo-4,7-dihydro-1,3-
benzothiazole-2-carboxamide]

Red powder. Melting point=174-175° C.
NMR $^1$H (DMSO d6, 400 MHz, δ): 9.63 (t, 2H, 2NH); 8.18 (t, 2H, 2NH); 7.27-7.25 (d, 4H); 6.88-6.85 (d, 4H); 5.54 (s, 2H, 2CH); 4.37-4.35 (d, 4H); 3.71 (s, 6H, 2CH$_3$); 3.24-3.20 (m, 4H); 2.41-2.38 (m, 4H); 2.17 (s, 3H, CH$_3$); 1.77-1.74 (m, 4H).
MS-LC: MH+=798.46; r.t.=8.89 min.

Example 34

5,5'-[(methylimino)bis(propane-3,1-diylimino)]
bis{2-[(6-methoxy-3,4-dihydroquinolin-1(2H)-yl)
carbonyl]-1,3-benzothiazole-4,7-dione}

Red powder. Melting point=159-160° C.
NMR $^1$H (DMSO d6, 400 MHz, δ): 8.15 (m, 2H, 2NH); 6.79-6.68 (m, 6H); 5.52 (s, 2H, 2CH); 4.15-4.12 (m, 4H); 3.72 (s, 6H, 2CH$_3$); 3.24-3.20 (m, 4H); 2.81-2.77 (m, 4H); 2.42-2.39 (m, 4H); 2.19 (s, 3H, CH$_3$); 2.00-1.91 (m, 4H); 1.78-1.75 (m, 4H).
MS-LC: MH+=650.48; r.t.=9.12 min.

Example 35

5,5'-[(methylimino)bis(propane-3,1-diylimino)]bis
(N-cyclohexyl-4,7-dioxo-4,7-dihydro-1,3-benzothia-
zole-2-carboxamide)

Red powder. Melting point=145-146° C.
NMR $^1$H (DMSO d6, 400 MHz, δ): 8.90-8.88 (d, 2H, 2NH); 8.19 (t, 2H, 2NH); 5.54 (s, 2H, 2CH); 3.75-3.72 (m, 2H); 3.25-3.20 (m, 4H); 2.42-2.39 (m, 4H); 2.18 (s, 3H, CH$_3$); 1.78-1.71 (m, 12H); 1.61-1.07 (m, 12H).
MS-LC: MH+=722.51; r.t.=9.14 min.

Example 36

5,5'-[(methylimino)bis(propane-3,1-diylimino)]bis
(2-([4-(4-methoxybenzoyl)piperazin-1-yl]carbonyl)-
1,3-benzothiazole-4,7-dione)

Red powder. Melting point=202-203° C.
NMR $^1$H (DMSO d6, 400 MHz, δ): 8.18 (t, 2H, 2NH); 7.43-7.41 (m, 4H); 7.00-6.98 (m, 4H); 5.51 (s, 2H, 2CH); 4.29-4.47 (m, 4H); 3.79 (s, 6H, 2CH$_3$); 3.73-3.72 (m, 4H); 3.64-3.62 (m, 8H); 3.24-3.19 (m, 4H); 2.43-2.40 (m, 4H); 2.19 (s, 3H, CH$_3$); 1.79-1.75 (m, 4H).
MS-LC: MH+=964.50; r.t.=8.36 min.

Example 37

5,5'-[(methylimino)bis(propane-3,1-diylimino)]bis
(2-{[4-(2-furoyl)piperazin-1-yl]carbonyl}-1,3-ben-
zothiazole-4,7-dione)

Red powder. Melting point=173-174° C.
NMR $^1$H (DMSO d6, 400 MHz, δ): 8.20 (t, 2H, 2NH); 7.85 (s, 2H); 7.06 (s, 2H); 6.64 (s, 2H); 5.53 (s, 2H, 2CH); 4.33-4.32 (m, 4H); 3.82-3.77 (m, 12H); 3.25-3.21 (m, 4H); 2.44-2.41 (m, 4H); 2.20 (s, 3H, CH$_3$); 1.79-1.76 (m, 4H).
MS-LC: MH+=884.37; r.t.=8.04 min.

The compound of Example 38 is obtained in a similar way to that used for Example 26, with 6-methoxy-2-(2-naphthyl)-1,3-benzothiazol-4,7-dione replacing 5-methoxy-2-(morpholin-4-ylcarbonyl)-1,3-benzothiazol-4,7-dione in the last stage.

Example 38

6,6'-[(methylimino)bis(propane-3,1-diylimino)]bis
[2-(2-naphthyl)-1,3-benzothiazole-4,7-dione]

Red powder.
MS-LC: MH+=724.40; r.t.=9.57 min.

Example 39

6,6'-[(methylimino)bis(propane-3,1-diylimino)]bis
[2-(1,3-benzodioxol-5-yl)-1,3-benzothiazole-4,7-
dione]

39.1) 2-(1,3-benzodioxol-5-yl)-6-methoxy-1,3-ben-
zothiazole-4,7-dione:

39.1.1)
2-bromo-6-methoxy-1,3-benzothiazol-2-amine 20 g (111 mmol) of 6-methoxy-1,3-benzothiazol-2-amine is solubilized in 400 ml of acetonitrile, then 13.2 ml (III mmol; 1 equivalent) of tert-butyl nitrite and 29 g (130 mmol; 1.2 equivalent) of CuBr$_2$ are added to the reaction medium which is then maintained under stirring at 80° C. for 2 hours. The solvent is evaporated off under reduced pressure, then the residue is taken up in 250 ml of ethyl acetate and washed twice with 200 ml of water. The organic phase is dried over sodium sulphate, then the solvent is evaporated off under reduced pressure and 24 g (yield=89%) of 2-bromo-6-methoxy-1,3-benzothiazol-2-amine is obtained and is used without other purification in to the following stage.

MS-LC: MH+=243.98; r.t.=10.89 min.

39.1.2) 2-bromo-6-methoxy-7-nitro-1,3-benzothiazole 24 g (100 mmol) of 2-bromo-6-methoxy-1,3-benzothiazol-2-amine is dissolved in 30 ml of sulphuric acid at 0° C., then 30 ml of nitric acid (density 1.41) is added dropwise. Stirring is maintained for 30 minutes at 0° C. then for 1 hour at ambient temperature. After neutralization of the reaction mixture by a 35% solution of soda (13.5M), the product formed is extracted with 3 times 100 ml of dichloromethane. The organic phase is dried over sodium sulphate then the solvent evaporated off under reduced pressure and the solid thus obtained is taken up in dichloromethane, filtered and washed with a dichloromethane/heptane mixture 1:1. The mother liquors are purified by chromatography on a silica column (eluent: ethyl acetate/heptane mixture 1:1). 9.9 g (yield=35%) of 2-bromo-6-methoxy-7-nitro-1,3-benzothiazole is obtained in the form of orange-coloured powder.

MS-LC: MH+=288.75; r.t.=10.70 min.

39.1.3) 2-(1,3-benzodioxol-5-yl)-6-methoxy-7-nitro-1,3-benzothiazole 0.697 g (4.2 mmol; 1.1 equivalent) of 1,3-benzodioxol-5-yl boronic acid as well as a solution of 1.2 g (11.35 mmol; 3 equivalents) of sodium carbonate in 15 ml of water are added to a suspension of 1.1 g (3.82 mmol) of 2-bromo-6-methoxy-7-nitro-1,3-benzothiazole and 133 mg (0.115 mmol; 0.03 equivalent) of palladium tetrakis-triphenylphosphine in 30 ml of 1,2-dimethoxyethane. The reaction mixture is maintained under stirring at 90° C. for 4 hours, then after concentration under reduced pressure, 100 ml of ethyl acetate is added to the medium which is then washed with twice 75 ml of a solution of water saturated with sodium chloride. The organic phase is dried over sodium sulphate then the solvents are evaporated off under reduced pressure and the residue is purified by chromatography on a silica column (eluent: ethyl acetate/heptane mixture 1:2). 0.960 g (yield of 76%) of 2-(1,3-benzodioxol-5-yl)-6-methoxy-7-nitro-1,3-benzothiazole is obtained in the form of beige powder.

MS-LC: MH+=331.06; r.t.=11.38 min.

39.1.4) 2-(1,3-benzodioxol-5-yl)-6-methoxy-1,3-benzothiazole-7-amine 0.96 g (2.9 mmol) of 2-(1,3-benzodioxol-5-yl)-6-methoxy-7-nitro-1,3-benzothiazole is suspended in 100 ml of methanol. 96 mg (10%) of palladium on carbon is added to the reaction mixture which is maintained under stirring under 2.5 bars of hydrogen for 18 hours. The catalyst is filtered out, then the solvents are evaporated off under reduced pressure. 0.45 g (yield=52%) of 2-(1,3-benzodioxol-5-yl)-6-methoxy-1,3-benzothiazol-7-amine is obtained and used in the following stage without other purification.

MS-LC: MH+=301.10; r.t.=10.48 min.

39.1.5) 2-(1,3-benzodioxol-5-yl)-6-methoxy-1,3-benzothiazol-4,7-dione 1.45 g (2.7 mmol; 1.8 equivalent) of Fremy's salt dissolved in 45 ml of a 0.3 M solution of sodium hydrogen phosphate is added to 0.45 g (1.5 mmol) of 2-(1,3-benzodioxol-5-yl)-6-methoxy-1,3-benzothiazol-7-amine in solution in 15 ml of acetone. The reaction mixture is maintained under stirring at ambient temperature for 5 hours then concentrated under reduced pressure. The product formed is extracted with 3 times 50 ml of dichloromethane and the aqueous phase is washed with 50 ml of a solution of water saturated with sodium chloride. The organic phases are combined, dried over sodium sulphate and the solvent evaporated off under reduced pressure. The expected product is purified by chromatography on a silica column (eluent: dichloromethane/methanol mixture 95:5). 0.2 g (yield=43%) of 2-(1,3-benzodioxol-5-yl)-6-methoxy-1,3-benzothiazol-4,7-dione is obtained in the form of a yellow powder.

MS-LC: MH+=316.07; r.t.=10.14 min.

39.2) 6,6'-[(methylimino)bis(propane-3,1-diylimino)]bis[2-(1,3-benzodioxol-5-yl)-1,3-benzothiazole-4,7-dione]

The experimental protocol is the same as that described for Example 26, with 2-(1,3-benzodioxol-5-yl)-6-methoxy-1,3-benzothiazol-4,7-dione replacing 5-methoxy-2-(morpholin-4-ylcarbonyl)-1,3-benzothiazol-4,7-dione in the last stage.

Red powder.

MS-LC: MH+=712.45; r.t.=8.57 min.

The compound of Example 40 is obtained in a similar way to that used for Example 1, with 2-(4-ethylphenyl)-6-methoxy-1,3-benzoxazole-4,7-dione replacing 5-methoxy-2-methyl-4,7-dioxobenzothiazole.

Example 40

6,6'-[(methylimino)bis(propane-3,1-diylimino)]bis[2-(4-ethylphenyl)-1,3-benzoxazole-4,7-dione]

Red powder. Melting point=216-217° C.
NMR $^1$H (CF$_3$COOD, 400 MHz, δ): 7.88-7.86 (d, 4H); 7.24-7.22 (d, 4H); 3.33-3.31 (m, 6H); 3.19-3.14 (m, 2H); 2.83 (s, 3H, CH$_3$); 2.57-2.51 (q, 4H, 2CH$_2$); 2.13-2.09 (m, 4H); 1.06-1.02 (t, 6H, 2CH$_3$).

MS-LC: MH+=648.35; r.t.=8.81 min.

Example 41

N-(4-methoxyphenyl)-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide

41.1) 5-({3-[(3-aminopropyl)(methyl)amino]propyl}amino)-2-methyl-1,3-benzothiazole-4,7-dione 1.6 g (7.65 mmol) of 5-methoxy-2-methyl-1,3-benzothiazole-4,7-dione is solubilized in 250 ml of dichloromethane. 6.17 ml (38.3 mmol; 5 equivalents) of N-(3-aminopropyl)-N-methylpropane-1,3-diamine is added and the reaction mixture is maintained for 2 hours under stirring at ambient temperature, then washed with 3 times 100 ml of water. The organic phases are combined, dried over sodium sulphate and the solvent is evaporated off under reduced pressure.

The desired product is obtained in the form of a red oil and is used in the following stage without other purification.

NMR $^1$H (DMSO d6, 400 MHz, δ): 5.45 (s, 1H); 3.21-3.17 (t, 2H); 2.75 (s, 3H, CH$_3$); 2.72-2.61 (m, 2H); 2.37-2.30 (m, 4H); 2.13 (s, 3H, CH$_3$); 1.73-1.69 (m, 2H); 1.55-1.52 (m, 2H).

MS-LC: MH+=323.21; r.t.=6.96 min.

41.2) 5-methoxy-N-(4-methoxyphenyl)-4,7-dioxo-4,7-dihydro-1,3-benzothiazole-2-carboxamide The experimental protocol is the same as that described for Stage 26.2.1, with 4-(methoxyphenyl)amine replacing morpholine.

NMR $^1$H (DMSO d6, 400 MHz, δ): 11.03 (s, 1H, NH); 7.79-7.75 (d, 2H); 6.97-6.93 (d, 2H); 6.37 (s, 1H); 3.90 (s, 3H, CH$_3$); 3.75 (s, 3H, CH$_3$).

MS-LC; MH+=345.08; r.t.=10.07 min.

41.3) N-(4-methoxyphenyl)-5-{[3-(methyl(3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide 5-({3-[(3-aminopropyl)(methyl)amino]propyl}amino)-2-methyl-1,3-benzothiazole-4,7-dione is solubilized in 250 ml of ethanol and 2.12 g (6.16 mmol; 0.8 equivalent) of 5-methoxy-N-(4-methoxyphenyl)-4,7-dioxo-4,7-dihydro-1,3-benzothiazole-2-carboxamide is added. The reaction mixture is maintained under stirring at 60° C. for 4 hours, then the solvent is evaporated off under reduced pressure. The residue is then purified by chromatography on a silica column (eluent: dichloromethane/methanol: 95/5) and 450 mg (yield=9%) of N-(4-methoxyphenyl)-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide is obtained in the form of red powder.

Melting point=141-142° C.

NMR $^1$H (DMSO d6, 400 MHz, δ): 10.87 (s, 1H, NH); 8.26 (t, 1H, NH); 7.92 (t, 1H, NH); 7.78-7.77 (d, 2H); 6.97-6.95 (d, 2H); 5.56 (s, 1H); 5.39 (s, 1H); 3.76 (s, 3H, CH$_3$); 3.25-3.15 (2m, 4H); 2.67 (s, 3H, CH$_3$); 2.43-2.38 (m, 4H); 2.18 (s, 3H, CH$_3$); 1.79-1.75 (m, 4H).

MS-LC: MH+=635.21; r.t.=8.31 min.

Transition to the Methanesulphonate:

The experimental protocol uses methods known to a person skilled in the art.

The salified compound precipitates in the form of a red powder.

The compounds of Examples 42 to 48 are obtained in a similar way to that used for Example 41, with 6-methoxy-2-methyl-1,3-benzothiazole-4,7-dione replacing 5-methoxy-2-methyl-1,3-benzothiazole-4,7-dione in the first stage of Example 42 and the suitable amine replacing 4-(methoxyphenyl)amine in the second stage.

Example 42

5-{[3-(methyl{3-[(2-methyl-4,7-dioxo-4,7-dihydro-1,3-benzothiazol-6-yl)amino]propyl}amino)propyl]amino}-2-{[4-(tetrahydrofuran-2-ylcarbonyl)piperazin-1-yl]carbonyl}-1,3-benzothiazole-4,7-dione Red powder. Melting point=121-122° C.

NMR $^1$H (DMSO d6, 400 MHz, δ): 8.24 (m, 1H, NH); 7.78 (t, 1H, NH); 5.53 (s, 1H); 5.31 (s, 1H); 4.70 (t, 1H); 4.18-4.35 (m, 2H); 3.55-3.80 (m, 8H); 3.24-3.16 (2m, 4H); 3.03-2.99 (m, 4H); 2.75 (s, 3H, CH$_3$); 2.42-2.40 (m, 4H); 2.18 (s, 3H, CH$_3$); 2.08-1.98 (m, 2H); 1.78-1.76 (m, 2H).

MS-LC: MH+=696.40; r.t.=7.49 min.

Example 43

N-ethyl-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide Red powder. Melting point=107-108° C.

NMR $^1$H (DMSO d6, 400 MHz, δ): 9.16 (t, 1H, NH); 8.17 (t, 1H, NH); 7.93 (t, 1H, NH); 5.53 (s, 1H); 5.40 (s, 1H); 3.22-3.19 (m, 4H); 3.01-2.99 (m, 2H); 2.71 (s, 3H, CH$_3$); 2.42-2.40 (m, 2H); 2.18 (s, 3H, CH$_3$); 1.77-1.72 (m, 6H); 1.13 (t, 3H, CH$_3$).

MS-LC: MH+=557.15; r.t.=7.68 min.

Example 44

5-({3-[(3-{[4,7-dioxo-2-(pyrrolidin-1-ylcarbonyl)-4,7-dihydro-1,3-benzothiazol-6-yl]amino}propyl)(methyl)amino]propyl}amino)-2-methyl-1,3-benzothiazole-4,7-dione Red powder.

NMR $^1$H (DMSO d6, 400 MHz, δ): 7.92 (t, 1H, NH); 7.75 (t, 1H, NH); 5.48 (s, 1H); 5.39 (s, 1H); 4.00 (t, 2H); 3.55 (t, 2H); 3.21-3.15 (m, 4H); 2.71 (s, 3H, CH$_3$); 2.42-2.40 (m, 4H); 2.18 (s, 3H, CH$_3$); 1.98-1.93 (m, 2H); 1.90-1.84 (m, 2H); 1.78-1.75 (m, 4H).

MS-LC: MH+=583.27; r.t.=7.74 min.

Example 45

N-(4-methoxybenzyl)-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide Red powder.

NMR $^1$H (DMSO d6, 400 MHz, δ): 9.65 (t, 1H, NH); 8.17 (t, 1H, NH); 7.94 (t, 1H, NH); 7.28-7.26 (d, 2H); 6.89-6.87 (d, 2H); 5.53 (s, 1H); 5.40 (s, 1H); 4.38-4.37 (d, 2H, CH$_2$); 3.72 (s, 3H, CH$_3$); 3.22-3.18 (m, 4H); 3.01-2.99 (m, 2H); 2.69 (s, 3H, CH$_3$); 2.42-2.40 (m, 2H); 2.18 (s, 3H, CH$_3$); 1.77-1.72 (m, 6H).

MS-LC: MH+=649.31; r.t.=8.28 min.

Example 46

N-1,3-benzodioxol-5-yl-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide Red powder.

MS-LC: MH+=649.36; r.t.=8.42 min.

Example 47

2-[(6-methoxy-3,4-dihydroquinolin-1(2H)-yl)carbonyl]-5-{[3-(methyl{3-[(2-methyl-4,7-dioxo-4,7-dihydro-1,3-benzothiazol-5-yl)amino]propyl}amino)propyl]amino}-1,3-benzothiazole-4,7-dione Red powder,
MS-LC: MH+=675.33; r.t.=8.40 min.

Example 48

2-{[4-(4-methoxybenzoyl)piperazin-1-yl]carbonyl}-5-{[3-(methyl{3-[(2-methyl-4,7-dioxo-4,7-dihydro-1,3-benzothiazol-5-yl)amino]propyl}amino)propyl]amino}-1,3-benzothiazole-4,7-dione Red powder.
NMR $^1$H (DMSO d6, 400 MHz, δ): 8.26 (t, 1H, NH); 7.89 (t, 1H, NH); 7.44-7.42 (d, 2H); 7.01-6.99 (d, 2H); 5.52 (s, 1H); 5.36 (s, 1H); 4.28-4.27 (m, 2H); 3.80 (s, 3H, CH$_3$); 3.74-3.64 (m, 4H); 3.22-3.14 (m, 6H); 2.69 (s, 3H, CH$_3$); 2.44-2.40 (m, 4H); 2.19 (s, 3H, CH$_3$); 1.78-1.75 (m, 4H).
MS-LC: MH+=732.32; r.t.=8.01 min.

Example 49

5-({3-[(3-{[2-(4-methoxyphenyl)-4,7-dioxo-4,7-dihydro-1,3-benzothiazol-6-yl]amino}propyl)(methyl)amino]propyl}amino)-2-methyl-1,3-benzothiazole-4,7-dione

49.1) 6-methoxy-2-(4-methoxyphenyl)-1,3-benzothiazole-4,7-dione

The experimental protocol is the same as that described for intermediate 39.1, with 4-methoxyphenyl boronic acid replacing 1,3-benzodioxol-5-yl boronic acid in the third stage.
MS-LC: MH+=302.10; r.t.=10.29 min.

49.2) 5-({3-[(3-{[2-(4-methoxyphenyl)-4,7-dioxo-4,7-dihydro-1,3-benzothiazol-6-yl]amino}propyl)(methyl)amino]propyl}amino)-2-methyl-1,3-benzothiazole-4,7-dione The experimental protocol is the same as that described for Example 41, with 6-methoxy-2-(4-methoxyphenyl)-1,3-benzothiazole-4,7-dione replacing 5-methoxy-N-(4-methoxyphenyl)-4,7-dioxo-4,7-dihydro-1,3-benzothiazole-2-carboxamide in the last stage.
Red powder.
MS-LC: MH+=592.35; r.t.=8.25 min.

Example 50

5-({3-[{3-[(4,7-dioxo-4,7-dihydro-1,3-benzothiazol-5-yl)amino]propyl}(methyl)amino]propyl}amino)-2-methyl-1,3-benzothiazole-4,7-dione The experimental protocol is the same as that described for Example 41, with 5-methoxy-1,3-benzothiazol-4,7-dione replacing 5-methoxy-N-(4-methoxyphenyl)-4,7-dioxo-4,7-dihydro-1,3-benzothiazole-2-carboxamide in the last stage.
Red powder.
NMR $^1$H (DMSO d6, 400 MHz, δ): 9.28 (s, 1H); 8.02 (t, 1H, NH); 7.95 (t, 1H, NH); 5.46 (s, 1H); 5.41 (s, 1H); 3.21-3.18 (m, 4H); 2.72 (s, 3H, CH$_3$); 2.41-2.38 (m, 4H); 2.18 (s, 3H, CH$_3$); 1.77-1.74 (m, 4H).
MS-LC: MH+=486.23; r.t.=7.45 min.

Example 51

2-(2,5-difluorophenyl)-6-{[3-(methyl{3-[(2-methyl-4,7-dioxo-4,7-dihydro-1,3-benzothiazol-5-yl)amino]propyl}amino)propyl]amino}-1,3-benzoxazole-4,7-dione The experimental protocol is the same as that described for Example 41, with 2-(2,5-difluorophenyl)-6-methoxy-1,3-benzoxazole-4,7-dione replacing 5-methoxy-N-(4-methoxyphenyl)-4,7-dioxo-4,7-dihydro-1,3-benzothiazole-2-carboxamide in the last stage.
Melting point=149-150° C.
NMR $^1$H (DMSO d6, 400 MHz, δ): 8.03 (t, 1H, NH); 7.93-7.88 (m, 2H); 7.61-7.58 (m, 2H); 5.39 (s, 1H); 5.33 (s, 1H); 3.21-3.15 (m, 4H); 2.68 (s, 3H, CH$_3$); 2.43-2.38 (m, 4H); 2.18 (s, 3H, CH$_3$); 1.78-1.75 (m, 4H).
MS-LC: MH+=582.22; r.t.=8.14 min.
Transition to the Methanesulphonate:
0.378 g (0.65 mmol) of 2-(2,5-difluorophenyl)-6-{[3-(methyl{3-[(2-methyl-4,7-dioxo-4,7-dihydro-1,3-benzothiazol-5-yl)amino]propyl}amino)propyl]amino}-1,3-benzoxazole-4,7-dione is solubilized in 50 ml of acetone and 46.4 μl (0.7 mmol; 1.1 equivalent) of methanesulphonic acid is added dropwise. The methanesulphonate precipitates in the form of a red powder. Melting point=99-100° C.
NMR $^1$H (D$_2$O, 400 MHz, δ): 7.58 (m, 1H); 7.47 (m, 1H); 7.37-7.31 (m, 1H); 5.21 (s, 1H); 5.08 (s, 1H); 3.35-3.21 (m, 8H); 2.91 (s, 3H, CH$_3$); 2.74 (s, 3H, CH$_3$); 2.51 (s, 3H, CH$_3$); 2.09-2.06 (m, 4H).
MS-LC: MH+=582.34; r.t.=8.45 min.

Example 52

2-(4-ethylphenyl)-6-{[3-(methyl{3-[(2-methyl-4,7-dioxo-4,7-dihydro-1,3-benzothiazol-5-yl)amino]propyl}amino)propyl]amino}-1,3-benzoxazole-4,7-dione The experimental protocol is the same as that described for Example 41, with 2-(4-ethylphenyl)-6-methoxy-1,3-benzoxazole-4,7-dione replacing 5-methoxy-N-(4-methoxyphenyl)-4,7-dioxo-4,7-dihydro-1,3-benzothiazole-2-carboxamide in the last stage.
NMR $^1$H (DMSO d6, 400 MHz, δ): 8.03-8.01 (d, 2H); 7.90-8.00 (2m, 2H, 2NH); 7.48-7.46 (d, 2H); 5.40 (s, 1H); 5.28 (s, 1H); 3.20-3.17 (m, 4H); 2.73-2.68 (q, 2H); 2.65 (s, 3H, CH$_3$); 2.42-2.40 (m, 4H); 2.19 (s, 3H, CH$_3$); 1.78-1.75 (m, 4H); 1.24 (t, 3H, CH$_3$).
MS-LC: MH+=574.24; r.t.=8.40 min.

Example 53

2-(2,5-difluorophenyl)-6-{[3-(methyl{3-[(2-methyl-4,7-dioxo-4,7-dihydro-1,3-benzothiazol-6-yl)amino]propyl}amino)propyl]amino}-1,3-benzoxazole-4,7-dione The experimental protocol is the same as that described for Example 41, with 6-methoxy-2-methyl-1,3-benzothiazole-4,7-dione replacing 5-methoxy-2-methyl-1,3-benzothiazole-4, 7-dione in the first stage and 2-(2,5-difluorophenyl)-6-methoxy-1,3-benzoxazole-4,7-dione replacing 5-methoxy-N-(4-methoxyphenyl)-4,7-dioxo-4,7-dihydro-1,3-benzothiazole-2-carboxamide in the last stage.

Red powder.

NMR $^1$H (DMSO d6, 400 MHz, δ): 8.03 (t, 1H, NH); 7.91 (m, 1H); 7.80 (t, 1H, NH); 7.61-7.59 (m, 2H); 5.34 (s, 1H); 5.33 (s, 1H); 3.21-3.17 (m, 4H); 2.72 (s, 3H, CH$_3$); 2.42-2.38 (m, 4H); 2.18 (s, 3H, CH$_3$); 1.78-1.74 (m, 4H).

MS-LC: MH+=582.31; r.t.=8.07 min.

Example 54

5.5'-[[(4-methoxybenzyl)imino]bis(propane-3,1-diylimino)]bis(2-methyl-1,3-benzothiazole-4,7-dione)

54.1) 5-[(3-bromopropyl)amino]-2-methyl-1,3-benzothiazole-4,7-dione 1.57 g (7.17 mmol; 1.5 equivalent) of 3-bromopropylamine hydrobromide and 1.02 ml (7.17 mmol; 1.5 equivalent) of triethylamine are added to 1 g (4.78 mmol) of 5-methoxy-2-methyl-1,3-benzothiazole-4,7-dione in solution in 100 ml of methanol. The reaction mixture is maintained under stirring for 2 hours at 60° C., then the solvent is evaporated off under reduced pressure and the residue is purified by chromatography on a silica column (eluent: dichloromethane/methanol: 97/3). The 5-[(3-bromopropyl)amino]-2-methyl-1,3-benzothiazole-4,7-dione is obtained in the form of a red oil.

MS-LC: MH+=314.99; r.t.=9.13 min.

54.2) 5-({3-[(4-methoxybenzyl)amino]propyl}amino)-2-methyl-1,3-benzothiazole-4,7-dione 160 μl (1.22 mmol; 1.1 equivalent) of 4-methoxybenzylamine, 213 μl (1.22 mmol; 1.1 equivalent) of diisopropylethylamine and a spatula tip's worth of sodium iodide are added to 0.35 g (1.11 mmol) of 5-[(3-bromopropyl)amino]-2-methyl-1,3-benzothiazole-4,7-dione in solution in 15 ml of dimethylformamide. The reaction mixture is maintained under stirring under microwaves for 5 minutes at 180° C. Then the solvent is evaporated off under reduced pressure and the reaction residue is taken up in dichloromethane, followed by washing with 3 times 50 ml of water. The organic phases are combined, dried over magnesium sulphate and the solvent is evaporated off under reduced pressure. The expected product is purified by chromatography on a silica column (eluent: dichloromethane/methanol: 95/5) and obtained in the form of a red oil.

MS-LC: MH+=372.15; r.t.=7.64 min.

54.3) 5.5'-[[(4-methoxybenzyl)imino]bis(propane-3,1-diylimino)]bis(2-methyl-1,3-benzothiazole-4,7-dione)

22 μl (128 μmol; 2 equivalents) of diisopropylethylamine, 21 mg (64 μmol; 1 equivalent) of 5-[(3-bromopropyl)amino]-2-methyl-1,3-benzothiazole-4,7-dione and a spatula tip's worth of sodium iodide are added to 23.6 mg (64 μmol) of 5-({3-[(4-methoxybenzyl)amino]propyl}amino)-2-methyl-1,3-benzothiazole-4,7-dione dissolved in 5 ml of acetonitrile. The reaction mixture is maintained under stirring under microwaves at 165° C. for 15 minutes, then the solvent is evaporated off under reduced pressure and the reaction residue is taken up in dichloromethane, followed by washing with 3 times 50 ml of water. The organic phases are combined, dried over magnesium sulphate and the solvent is evaporated off under reduced pressure. The expected product is purified by chromatography on a silica column (eluent: dichloromethane/methanol: 93/7) and obtained in the form of a red oil.

MS-LC: MH+=606.23; r.t.=7.95 min.

Example 55

5.5'-[(methylimino)bis(butane-4,1-diylimino)]bis(2-methyl-1,3-benzothiazole-4,7-dione)

55.1) tert-butyl[4-(1,3-dioxo-1,3-dihydro-2H-isoindol-2-yl)butyl]methylcarbamate 2 g (9.9 mmol) of tert-butyl(4-aminobutyl)methylcarbamate and 1.46 g (9.9 mmol; 1 equivalent) of 2-benzofuran-1,3-dione are solubilized in 50 ml of toluene and the reaction mixture is maintained under reflux for 24 hours in a Dean-Stark. The solvent is evaporated off under reduced pressure and the expected product is purified on a silica column (eluent: dichloromethane/methanol: 90/10).

MS-LC: MH+=333.26; r.t.=10.90 min.

55.2) 2-[4-(methylamino)butyl]-1H-isoindole-1.3(2H)-dione 0.6 g (1.8 mmol) of tert-butyl[4-(1,3-dioxo-1,3-dihydro-2H-isoindol-2-yl)butyl]methylcarbamate is solubilized in 865 ml (10.8 mmol; 6 equivalents) of trifluoromethanesulphonic acid and the reaction mixture is maintained under stirring for 2 hours at ambient temperature. The solvents are evaporated off, then the excess acid is coevaporated with 3 times 50 ml of dichloromethane. The expected product is used without other purification in the following stage.

MS-LC: MH+=233.19; r.t.=7.38 min.

55.3) 2.2'-[(methylimino)dibutane-4,1-diyl]bis(1H-isoindole-1.3(2H)-dione)

209 mg (0.9 mmol) of 2-[4-(methylamino)butyl]-1H-isoindole-1.3(2H)-dione is solubilized in 5 ml of tetrahydrofuran, then 385 μl (2.7 mmol; 3 equivalents) of triethylamine and 254 mg (0.9 mmol; 1 equivalent) of 2-(4-bromobutyl)-1H-isoindole-1.3(2H)-dione are added to the reaction mixture which is maintained for 25 minutes under microwaves at 165° C. The precipitate obtained is filtered and the filtrate concentrated under reduced pressure. The expected product is purified by chromatography on a silica column (eluent: dichloromethane/methanol: 95/5).

MS-LC: MH+=434.25; r.t.=8.37 min.

55.4) N-(4-aminobutyl)-N-methylbutane-1,4-diamine 144 mg (0.33 mmol) of 2.2'-[(methylimino)dibutane-4,1-diyl]bis(1H-isoindole-1.3(2H)-dione) is solubilized in 2 ml of ethanol and 65 μl (0.73 mmol; 2.2 equivalents) of 35% hydrazine hydrate are added to the reaction mixture which is maintained under stirring at 150° C. under microwaves for 30 minutes. The solvents are evaporated off under reduced pressure and the excess hydrazine hydrate is eliminated by co-evaporation with 4 times 15 ml of ethanol. 100 ml of ethanol is added to the reaction mixture which is acidified to pH 1 with a 1N solution of hydrochloric acid in ethyl ether. The reaction medium is concentrated under reduced pressure, then taken up in 50 ml of ethanol and the white precipitate formed is filtered, washed with 3 times 20 ml of water and eliminated. The filtrate is basified to pH 12 with a 2M solution of soda, then concentrated under reduced pressure and used in the following stage without other purification.

NMR $^1$H (DMSO d6, 400 MHz, δ): 3.13-3.10 (m, 4H); 2.24-2.20 (m, 4H); 2.08 (s, 3H, CH$_3$); 1.38-1.34 (m, 4H).

MS-LC: MH+=174.29; r.t.=8.99 min.

55.5) 5.5'-[(methylimino)bis(butane-4,1-diylimino)] bis(2-methyl-1,3-benzothiazole-4,7-dione)

6 mg (34 μmol) of N-(4-aminobutyl)-N-methylbutane-1,4-diamine is added to a solution of 15 mg (71 mmol; 2.1 equivalents) of 5-methoxy-2-methyl-1,3-benzothiazole-4,7-dione in 1.5 ml of ethanol, then the reaction mixture is stirred at 60° C. for 1 hour. The solvent is then evaporated off under reduced pressure and the expected product is obtained by purification by chromatography on a silica column (eluent: dichloromethane/methanol: 95/5) in the form of a red oil.

MS-LC: MH+=527.69; r.t.=10.13 min.

Example 56

2-methyl-5-{[3-(methyl{4-[(2-methyl-4,7-dioxo-4,7-dihydro-1,3-benzothiazol-5-yl)amino]butyl}amino) propyl]amino}-1,3-benzothiazole-4,7-dione

56.1) 2-(3-[[4-(1,3-dioxo-1,3-dihydro-2H-isoindol-2-yl)butyl](methyl)amino]propyl)-1H-isoindole-1.3 (2H)-dione The experimental protocol is the same as that described for Example 55.3, with 2-(3-bromopropyl)-1H-isoindole-1.3 (2H)-dione replacing 2-(4-bromobutyl)-1H-isoindole-1.3 (2H)-dione.

MS-LC: MH+=420.24; r.t.=8.19 min.

56.2) N-(3-aminopropyl)-N-methylbutane-1,4-diamine

The experimental protocol is the same as that described for Example 55.4.

56.3) 2-methyl-5-{[3-(methyl(4-[(2-methyl-4,7-dioxo-4,7-dihydro-1,3-benzothiazol-5-yl)amino]butyl) amino)propyl]amino}-1,3-benzothiazole-4,7-dione The experimental protocol is the same as that described for Example 55.5, with N-(3-aminopropyl)-N-methylbutane-1,4-diamine replacing N-(4-aminobutyl)-N-methylbutane-1,4-diamine.

Pharmacological Study of the Compounds of the Invention

Test Protocols i) Measurement of the Phosphatase Activity of the Purified Recombinant Enzyme Cdc25C The phosphatase activity of the protein MBP-Cdc25C is evaluated by the dephosphorylation of 3-O-methylfluorescein-phosphate (OMFP) to 3-O-methylfluorescein (OMF) with a determination of the fluorescence at 475 nm of the reaction product. This test makes it possible to identify inhibitors of the recombinant enzyme cdc25. The preparation of the fusion protein MBP-Cdc25C is described in the Patent Application PCT WO 01/44467.

The reaction is carried out in 384-well plate format at a final volume of 50 μl. The protein MBP-Cdc25C (prepared as described above) is preserved in the following elution buffer: 20 mM Tris-HCl pH 7.4; 250 mM NaCl; 1 mM EDTA; 1 mM of dithiothreitol (DTT); 10 mM maltose. It is diluted to a concentration of 60 μM in the following reaction buffer: 50 mM Tris-HCl pH 8.2; 50 mM NaCl; 1 mM DTT; 20% glycerol. Measurement of the background noise is carried out with the buffer without the addition of the enzyme. The products are tested at decreasing concentrations starting from 40 μM. The reaction is initiated by the addition of an OMFP solution at 500 μM final (prepared extemporaneously from a 12.5 mM stock solution in 100% DMSO (Sigma #M2629)). After 4 hours at 30° C. in a single-use 384-well plate, the fluorescence measured at OD 475 nm is read using a Victor$^2$ plate reader (EGG-Wallac). The determination of the concentration inhibiting the enzyme reaction by 50% is calculated from three independent experiments. Only the values contained in the linear part of the sigmoid are retained for linear regression analysis.

ii) Characterization of Anti-Proliferative Activity:

By way of example, the effect of a treatment by the compounds of the examples described previously on two lines of human Mia-Paca2 and DU145 cells will be studied. The cell lines DU145 (human prostate cancer cells) and Mia-PaCa2 (human pancreatic cancer cells) were acquired from the American Tissue Culture Collection (Rockville, Md., USA). The cells placed in 80 μl of Dulbecco's Modified Eagle medium (Gibco-Brl, Cergy-Pontoise, France) completed with 10% foetal calf serum inactivated by heating (Gibco-Brl, Cergy-Pontoise, France), 50,000 units/l of penicillin and 50 mg/l streptomycin (Gibco-Brl, Cergy-Pontoise, France), and 2 mM of glutamine (Gibco-Brl, Cergy-Pontoise, France) were seeded on a 96-well plate on day 0. The cells were treated on day 1 for 96 hours at increasing concentrations of each of the compounds to be tested up to 10 μM. At the end of the of this period, quantification of the cell proliferation is evaluated by a colorimetric test based on the cleavage of the tetrazolium salt WST1 by the mitochondrial dehydrogenases in the viable cells leading to the formation of formazan (Boehringer Mannheim, Meylan, France). These tests are carried out in duplicate with 8 determinations per concentration tested. For each compound to be tested, the values included in the linear part of the sigmoid were retained for linear regression analysis and used in order to estimate the inhibitory concentration $IC_{50}$. The products are solubilized in dimethylsulphoxide (DMSO) at to $10^{-2}$M and finally used in culture with 0.1% DMSO.

Results of the Tests a) The compounds of Examples 1 to 5, 7, 8, 10, 14, 15, 17, 18, 20, 22, 25 to 28, 31 to 37, 41 to 45, 47, 48, 50, 51 and 53 have an $IC_{50}$ less than or equal to 1 μM on the phosphatase activity of the purified recombinant enzyme Cdc25-C. As regards the compounds of Examples 6, 11 and 23, they have an $IC_{50}$ less than or equal to 5 μM on the phosphatase activity of the purified recombinant enzyme Cdc25-C.

b) The compounds of Examples 1 to 8, 10, 11, 14, 15, 17, 18, 20, 22, 25 to 28, 31 to 37, 41 to 45, 48, 50, 51 and 53 have an $IC_{50}$ less than or equal to 10 μM on the cell proliferation of the Mia-Paca2 lines.

c) The compounds of Examples 1 to 8, 10, 11, 14, 15, 17, 18, 20, 22, 25, 26, 31 to 37, 41 to 45, 48, 50 and 53 have an $IC_{50}$ less than or equal to 10 μM on the cell proliferation of the DU-145 lines.

The invention claimed is:
1. A compound of general formula (I)

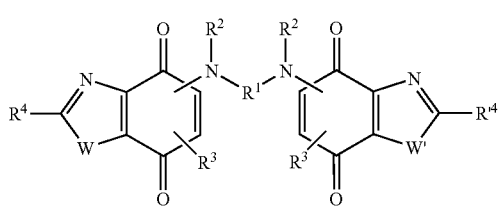

in racemic, enantiomeric form or any combination thereof, in which:

each of W and W' represents independently O or S;

$R^1$ represents one of —$CH_2$—$CR^6R^7$—$CH_2$—, —$(CH_2)_m$—X—$(CH_2)_n$—, —$(CH_2)_p$-[O—$(CH_2)_q]_r$—O—$(CH_2)_p$— or —$(CH_2)_s$—CO—$NR^8$—$(CH_2)_t$— in which m and n are each independently an integer from 2 to 6, p and t are each independently an integer from 2 to 12, q is an integer from 2 to 4, r is an integer from 0 to 4, s is an integer from 1 to 12, X is —$NR^5$—, —S—, —CO—, —$CR^6R^7$—, cycloalkyl or aryl, with the proviso that when X represents —S—, —CO—, —$CR^6R^7$—, cycloalkyl or aryl, m and n are equal, $R^5$ represents a hydrogen atom, alkyl, or arylalkyl radical optionally substituted by 1 to 3 substituents including a halogen atom, an alkyl, or alkoxy radical, $R^6$ and $R^7$ each independently represent a hydrogen atom or an alkyl radical and $R^8$ represents a hydrogen atom or an alkyl or arylalkyl radical, or $R^1$ represents

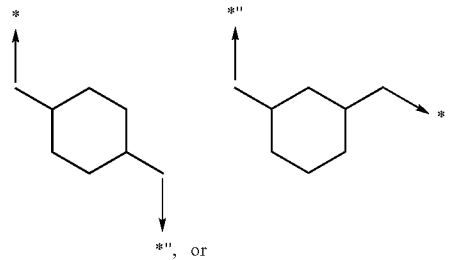

with the proviso that →* signifies the attachment point to the general formula (I);

or $R^1$ represents —$(CH_2)_w$—N(Y)—$(CH_2)_{w'}$— in which Y is

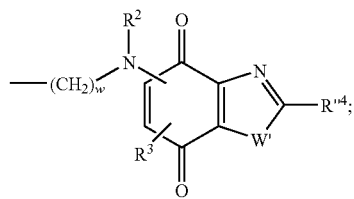

W" represents O or S and w is an integer from 2 to 3;

$R^2$ represents a hydrogen atom or an alkyl or arylalkyl radical;

$R^3$ represents a hydrogen atom or a halogen atom;

each of $R^4$, $R'^4$ and $R'''^4$ represents independently a hydrogen atom, an alkyl radical, an alkoxyalkyl radical, an aryloxyalkyl radical, a phenyl radical possessing two substituents which form together a methylenedioxy or ethylene dioxy radical, a —$CH_2$—$NR^9R^{10}$ radical, a —CO—$NR^{14}R^{15}$ radical, or a carbocyclic aryl or carbocyclic arylalkyl radical optionally substituted by 1 to 4 substituents including a halogen atom, alkyl, haloalkyl, alkoxy, haloalkoxy or aryl, or $R^4$ represents

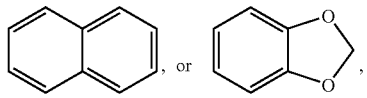

$R^9$ represents independently an alkyl radical and $R^{10}$ represents independently a hydrogen atom or an alkyl radical, or $R^9$ and $R^{10}$ form together with the nitrogen atom to which they are attached, a heterocycle with 4 to 7 members comprising 1 to 2 heteroatoms, the members necessary for completing the heterocycle including —$CR^{11}R^{12}$—, —O—, —S—, or —$NR^{13}$—, $R^{11}$ and $R^{12}$ represent independently a hydrogen atom or an alkyl radical and $R^{13}$ represents an alkyl or arylalkyl radical, or $R^{13}$ represents a phenyl radical optionally substituted by 1 to 3 substituents including a halogen atom, an alkyl or alkoxy radical, $R^{14}$ represents independently an alkyl radical, a haloalkyl radical, a cycloalkyl radical, a cycloalkylalkyl radical, an alkoxylalkyl radical, carbocyclic or heterocyclic aryl or carbocyclic or heterocyclic arylalkyl radicals, wherein the aryl ring is optionally substituted by 1 to 3 substituents including a halogen atom, an alkyl radical, an alkyl radical, an alkoxy radical, a haloalkyl radical or an —$SO_2$—$NH_2$ radical, or $R^{14}$ represents

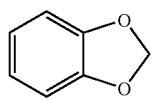

or $R^{14}$ represents —$(CH_2)_a$—[O—$(CH_2)_b]_c$—O-Alk, —$(CH_2)_d$—[O—$(CH_2)_e]_f$—$NR^{16}R^{17}$ or —$(CH_2)_g$-A radicals in which a, b and e are each independently an integer from 2 to 4, c is an integer from 1 to 4, f is an integer from 0 to 4, d is an integer from 2 to 12 and g is an integer from 1 to 12, Alk is an alkyl radical, $R^{16}$ is a hydrogen atom or an alkyl, alkoxycarbonyl or aralkoxycarbonyl radical, $R^{17}$ is a hydrogen atom or an alkyl radical and A is a saturated heterocycle substituted by 1 to 2 heteroatoms including O, N or S and attached to the group —$(CH_2)_g$— by N or CH, said saturated heterocycle comprising from 2 to 6 additional members including —$CHR^{18}$—, —CO—, —$NR^{19}$—, —O— or —S—, $R^{18}$ represents a hydrogen atom or an alkyl radical and $R^{19}$ represents a hydrogen atom, an alkyl radical or an alkoxycarbonyl or aralkoxycarbonyl group, and $R^{15}$ represents independently a hydrogen atom or an alkyl or arylalkyl radical, or $R^{15}$ represents a radical identical to $R^{14}$ when $R^{14}$ represents a carbocyclic or heterocyclic alkyl, haloalkyl, alkoxylalkyl or arylalkyl radical, wherein the aryl ring is optionally substituted by 1 to 3 substituents including a halogen atom, an alkyl radical, an alkoxy radical, a haloalkyl radical or an —SO$_2$—NH$_2$ radical or R$^{14}$ and R$^{15}$ form together with the nitrogen atom to which they are attached, a saturated heterocycle with 4 to 7 members comprising 1 to 2 heteroatoms, the members necessary for completing the heterocycle including —CR$^{20}$R$^{21}$—, —O—, —S— or —NR$^{22}$— radicals, R$^{20}$ and R$^{21}$ represent a hydrogen atom or an alkyl or arylalkyl radical and R$^{22}$ represents —COR$^{23}$ or —SO$_2$R$^{24}$, R$^{23}$ represents an alkyl radical, a carbocyclic aryl radical optionally substituted by 1 to 3 substituents including a halogen atom, an alkyl radical or an alkoxy radical, or R$^{23}$ represents a heterocyclic aryl radical or a saturated heterocycle including 5 to 7 members and 1 to 2 heteroatoms including O, N or S R$^{24}$ represents a hydrogen atom or an alkyl radical, or R$^{14}$ and R$^{15}$ form together with the nitrogen atom to which they are attached a heterocyclic aryl radical of the formulas

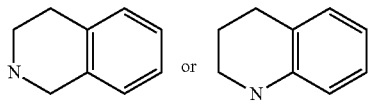

wherein the aromatic ring may be substituted by 1 to 3 substituents including an alkyl radical or an alkoxy radical;

with the proviso that when R' represents —(CH$_2$)$_w$—N(Y)—(CH$_2$)$_w$— radical, W, W' and W'' are, R$^4$, R'$^4$ and R''$^4$ are identical and the nitrogen atoms adjacent to the 1,3-benzothiazole-4,7-dione or 1,3-benzoxazole-4,7-dione rings are either each attached in position 5 of the corresponding 1,3-benzothiazole-4,7-dione or 1,3-benzoxazole-4,7-dione ring or are each attached in position 6 of the corresponding 1,3-benzothiazole-4,7-dione or 1,3-benzoxazole-4,7-dione ring;

or a pharmaceutically acceptable salt thereof.

2. The compound according to claim 1, wherein R' does not represent a —(CH$_2$)$_w$—N(Y)—(CH$_2$)$_w$— radical, W and W' are identical and R$^4$ and R'$^4$ are identical;

or a pharmaceutically acceptable salt thereof.

3. The compound according to claim 1 or 2, wherein R$^1$ represents CH$_2$—CR$^6$R$^7$—CH$_2$—, —(CH$_2$)$_m$—X—(CH$_2$)$_n$—, —(CH$_2$)$_r$—[O—(CH$_2$)$_q$]$_r$—O—(CH$_2$)$_p$— or (CH$_2$)$_s$—CO—NR$^8$—(CH$_2$)$_t$— radicals; or a pharmaceutically acceptable salt thereof.

4. The compound according to claim 1 or 2, wherein R' represents —(CH$_2$)$_m$—X—(CH$_2$)$_n$—; or a pharmaceutically acceptable salt thereof.

5. The compound according to claim 1, which is:
- -5.5'-[(methylimino)bis(propane-3,1-diylimino)]bis(2-methyl-1,3-benzothiazole-4,7-dione);
- -5.5'-[(methylimino)bis(ethane-2,1-diylimino)]bis(2-methyl-1,3-benzothiazole-4,7-dione);
- -5.5'-[oxybis(ethane-2,1-diylimino)]bis(2-methyl-1,3-benzothiazole-4,7-dione);
- -5.5'-(pentane-1,5-diyldiimino)bis(2-methyl-1,3-benzothiazole-4,7-dione);
- -6.6'-[(methylimino)bis(propane-3,1-diylimino)]bis(2-methyl-1,3-benzothiazole-4,7-dione);
- -6.6'-[(methylimino)bis(ethane-2,1-diylimino)]bis(2-methyl-1,3-benzothiazole-4,7-dione);
- -5.5'-[(methylimino)bis(propane-3,1-diylimino)]bis {4,7-dioxo-N-[3-(2-oxopyrrolidin-1-yl)propyl]-4,7-dihydro-1,3-benzothiazole-2-carboxamide};
- -6.6'-[(methylimino)bis(propane-3,1-diylimino)]bis[2-(2,5-difluorophenyl)-1,3-benzoxazole-4,7-dione];
- -6.6'-[(methylimino)bis(propane-3,1-diylimino)]bis[2-(3,5-dibromophenyl)-1,3-benzoxazole-4,7-dione];
- -6.6'-[(methylimino)bis(propane-3,1-diylimino)]bis[2-(2-chloro-6-fluorobenzyl)-1,3-benzoxazole-4,7-dione];
- -6.6'-[(methylimino)bis(propane-3,1-diylimino)]bis[2-(3-bromophenyl)-1,3-benzoxazole-4,7-dione];
- -6.6'-[(methylimino)bis(propane-3,1-diylimino)]bis[2-(4-bromophenyl)-1,3-benzoxazole-4,7-dione];
- -6.6'-[(methylimino)bis(propane-3,1-diylimino)]bis[2-(3,5-difluorophenyl)-1,3-benzoxazole-4,7-dione];
- -6.6'-[(methylimino)bis(propane-3,1-diylimino)]bis[2-(3-chlorophenyl)-1,3-benzoxazole-4,7-dione];
- -6.6'-[(methylimino)bis(propane-3,1-diylimino)]bis[2-(4-fluorophenyl)-1,3-benzoxazole-4,7-dione];
- -6.6'-[(methylimino)bis(propane-3,1-diylimino)]bis [2-(4-bromo-3-methylphenyl)-1,3-benzoxazole-4,7-dione];
- -5.5'-[(methylimino)bis(propane-3,1-diylimino)]bis(6-bromo-2-methyl-1,3-benzothiazole-4,7-dione);
- -5.5',5''-[nitrilotris(propane-3,1-diylimino)]tris(2-methyl-1,3-benzothiazole-4,7-dione);
- -5.5'-(2,2-dimethylpropane-1,3-diyldiimino)bis(2-methyl-1,3-benzothiazole-4,7-dione);
- -5.5'-[cyclohexane-1,4-diylbis(methyleneimino)]bis(2-methyl-1,3-benzothiazole-4,7-dione);
- -5.5'-[1,3-phenylenebis(methyleneimino)]bis(2-methyl-1,3-benzothiazole-4,7-dione);
- -5.5'-[ethane-1,2-diylbis(oxypropane-3,1-diylimino)]bis(2-methyl-1,3-benzothiazole-4,7-dione);
- -6.6'-{(methylimino)bis[propane-3,1-diyl(methylimino)]} bis[2-(2,5-difluorophenyl)-1,3-benzoxazole-4,7-dione];
- —N$^3$-[2-(2,5-difluorophenyl)-4,7-dioxo-4,7-dihydro-1,3-benzoxazol-6-yl]-N$^1$-(3-{[2-(2,5-difluorophenyl)-4,7-dioxo-4,7-dihydro-1,3-benzoxazol-6-yl]amino} propyl)-β-alaninamide;
- -5.5'-[(methylimino)bis(propane-3,1-diylimino)]bis(1,3-benzothiazole-4,7-dione);
- -5.5'-[(methylimino)bis(propane-3,1-diylimino)]bis [2-(morpholin-4-ylcarbonyl)-1,3-benzothiazole-4,7-dione];
- -5.5'-[(methylimino)bis(propane-3,1-diylimino)]bis(2-{[4-(morpholin-4-ylcarbonyl)piperazin-1-yl]carbonyl}-1,3-benzothiazole-4,7-dione);
- -5.5'-[(methylimino)bis(propane-3,1-diylimino)]bis(2-{[4-(tetrahydrofuran-2-ylcarbonyl)piperazin-1-yl]carbonyl}-1,3-benzothiazole-4,7-dione);
- -5.5'-[(methylimino)bis(propane-3,1-diylimino)]bis(2-{[4-(methylsulphonyl)piperazin-1-yl]carbonyl}-1,3-benzothiazole-4,7-dione);
- -5.5'-[(methylimino)bis(propane-3,1-diylimino)]bis [N-(4-methoxyphenyl)-4,7-dioxo-4,7-dihydro-1,3-benzothiazole-2-carboxamide];
- -6.6'-[(methylimino)bis(propane-3,1-diylimino)]bis [2-(pyrrolidin-1-ylcarbonyl)-1,3-benzothiazole-4,7-dione];
- -5.5'-[(methylimino)bis(propane-3,1-diylimino)]bis[N-(4-fluorophenyl)-4,7-dioxo-4,7-dihydro-1,3-benzothiazole-2-carboxamide];
- -5.5'-[(methylimino)bis(propane-3,1-diylimino)]bis[N-(4-methoxybenzyl)-4,7-dioxo-4,7-dihydro-1,3-benzothiazole-2-carboxamide];

- 5.5'-[(methylimino)bis(propane-3,1-diylimino)]bis{2-[(6-methoxy-3,4-dihydroquinolin-1(2H)-yl)carbonyl]-1,3-benzothiazole-4,7-dione};
- 5.5'-[(methylimino)bis(propane-3,1-diylimino)]bis(N-cyclohexyl-4,7-dioxo-4,7-dihydro-1,3-benzothiazole-2-carboxamide);
- 5.5'-[(methylimino)bis(propane-3,1-diylimino)]bis(2-{[4-(4-methoxybenzoyl)piperazin-1-yl]carbonyl}-1,3-benzothiazole-4,7-dione);
- 5.5'-[(methylimino)bis(propane-3,1-diylimino)]bis(2-{[4-(2-furoyl)piperazin-1-yl]carbonyl}-1,3-benzothiazole-4,7-dione);
- 6.6'-[(methylimino)bis(propane-3,1-diylimino)]bis[2-(2-naphthyl)-1,3-benzothiazole-4,7-dione];
- 6.6'-[(methylimino)bis(propane-3,1-diylimino)]bis [2-(1,3-benzodioxol-5-yl)-1,3-benzothiazole-4,7-dione];
- 6.6'-[(methylimino)bis(propane-3,1-diylimino)]bis[2-(4-ethylphenyl)-1,3-benzoxazole-4,7-dione];
- —N-(4-methoxyphenyl)-5-{[3-(methyl{3-[(2-methyl-4,7-dioxo-4,7-dihydro-1,3-benzothiazol-5-yl)amino]propyl}amino)propyl]amino}-4,7-dioxo-4,7-dihydro-1,3-benzothiazole-2-carboxamide;
- 5-{[3-(methyl{3-[(2-methy 1-4,7-dioxo-4,7-dihydro-1,3-benzothiazol-6-yl)amino]propyl}amino)propyl]amino}-2-{[4-(tetrahydrofuran-2-ylcarbonyl)piperazin-1-yl]carbonyl}-1,3-benzothiazole-4,7-dione;
- —N-ethyl-5-{[3-(methyl{3-[(2-methy 1-4,7-dioxo-4,7-dihydro-1,3-benzothiazol-5-yl)amino]propyl}amino)propyl]amino}-4,7-dioxo-4,7-dihydro-1,3-benzothiazole-2-carboxamide;
- 5-({3-[(3-{[4,7-dioxo-2-(pyrrolidin-1-ylcarbonyl)-4,7-dihydro-1,3-benzothiazol-6-yl]amino}propyl)(methyl)amino]propyl}amino)-2-methyl-1,3-benzothiazole-4,7-dione;
- —N-(4-methoxybenzyl)-5-{[3-(methyl{3-[(2-methyl-4,7-dioxo-4,7-dihydro-1,3-benzothiazol-5-y)amino]propyl}amino)propyl]amino}-4,7-dioxo-4,7-dihydro-1,3-benzothiazole-2-carboxamide;
- —N-1,3-benzodioxol-5-yl-5-{[3-(methyl{3-[(2-methy 1-4,7-dioxo-4,7-dihydro-1,3-benzothiazol-5-yl)amino]propyl}amino)propyl]amino}-4,7-dioxo-4,7-dihydro-1,3-benzothiazole-2-carboxamide;
- 2-[(6-methoxy-3,4-dihydroquinolin-1(2H)-yl)carbonyl]-5-{[3-(methyl{3-[(2-methyl-4,7-dioxo-4,7-dihydro-1,3-benzothiazol-5-yl)amino]propyl}amino)propyl]amino}-1,3-benzothiazole-4,7-dione;
- 2-{[4-(4-methoxybenzoyl)piperazin-1-yl]carbonyl}-5-{[3-(methyl{3-[(2-methy 1-4,7-dioxo-4,7-dihydro-1,3-benzothiazol-5-yl)amino]propyl}amino)propyl]amino}-1,3-benzothiazole-4,7-dione;
- 5-({3-[(3-{[2-(4-methoxyphenyl)-4,7-dioxo-4,7-dihydro-1,3-benzothiazol-6-yl]amino}propyl)(methyl)amino]propyl}amino)-2-methyl-1,3-benzothiazole-4,7-dione;
- 5-({3-[{3-[(4,7-dioxo-4,7-dihydro-1,3-benzothiazol-5-yl)amino]propyl}(methyl)amino]propyl}amino)-2-methyl-1,3-benzothiazole-4,7-dione;
- 2-(2,5-difluorophenyl)-6-{[3-(methyl{3-[(2-methy 1-4,7-dioxo-4,7-dihydro-1,3-benzothiazol-5-yl)amino]propyl}amino)propyl]amino}-1,3-benzoxazole-4,7-dione;
- 2-(4-ethylphenyl)-6-{[3-(methyl{3-[(2-methyl-4,7-dioxo-4,7-dihydro-1,3-benzothiazol-5-yl)amino]propyl}amino)propyl]amino}-1,3-benzoxazole-4,7-dione;
- 2-(2,5-difluorophenyl)-6-{[3-(methyl{3-[(2-methyl-4,7-dioxo-4,7-dihydro-1,3-benzothiazol-6-yl)amino]propyl}amino)propyl]amino}-1,3-benzoxazole-4,7-dione;
- 5.5'-[[(4-methoxybenzyl)imino]bis(propane-3,1-diylimino)]bis(2-methyl-1,3-benzothiazole-4,7-dione);
- 5.5'-[(methylimino)bis(butane-4,1-diylimino)]bis(2-methyl-1,3-benzothiazole-4,7-dione); or
- 2-methyl-5-{[3-(methyl{4-[(2-methyl-4,7-dioxo-4,7-dihydro-1,3-benzothiazol-5-yl)amino]butyl}amino)propyl]amino}-1,3-benzothiazole-4,7-dione;

or a pharmaceutically acceptable salt thereof.

6. A pharmaceutical composition comprising the compound according to claim 1 or a pharmaceutically acceptable salt thereof.

7. A pharmaceutical composition comprising, as an active ingredient, the compound according to claim 1 or a pharmaceutically acceptable salt thereof, with at least one pharmaceutically acceptable excipient.

8. A method of treating cancer comprising administering a compound according to claim 1, or a pharmaceutically acceptable salt thereof to a patient in need thereof wherein the cancer is prostate or pancreatic cancer.

9. The method according to claim 8, wherein the cancer is prostate cancer.

10. The method according to claim 8, wherein the cancer is pancreatic cancer.

11. The compound according to claim 1, wherein in the definition of $R^1$, m and n are each independently an integer from 2 to 4.

12. The compound according to claim 11, wherein m and n are each independently an integer from 2 to 3.

13. The compound according to claim 1, wherein in the definition of $R^1$, p and t are each independently an integer from 2 to 8.

14. The compound according to claim 13, wherein p and t are each independently an integer from 2 to 6.

15. The compound according to claim 1, wherein in the definition of $R^1$, q is an integer from 2 to 3.

16. The compound according to claim 1, wherein in the definition of $R^1$, r is an integer from 0 to 2.

17. The compound according to claim 1, wherein in the definition of $R^1$, s is an integer from 1 to 8.

18. The compound according to claim 17, wherein, s is an integer from 1 to 6.

19. The compound according to claim 1, wherein in the definition of $R^{14}$, d is an integer from 2 to 8.

20. The compound according to claim 19, wherein d is an integer from 2 to 6.

21. The compound according to claim 1, wherein in the definition of $R^{14}$, g is an integer from 1 to 8.

22. The compound according to claim 21, wherein g is an integer from 1 to 6.

23. The compound according to claim 1, wherein, $R^{23}$ is piperidino, piperazino, morpholino, thiomorpholino or 2-tetrahydrofuryl.

24. The compound according to claim 1, wherein $R^{24}$ is an alkyl radical.

* * * * *